(12) United States Patent
Sakaguchi et al.

(10) Patent No.: US 9,895,198 B2
(45) Date of Patent: Feb. 20, 2018

(54) MEDICAL MANIPULATOR WITH ATTACHMENT LIMITING MECHANISM INCLUDING COUNTING MECHANISM

(71) Applicant: Karl Storz SE & Co. KG, Tuttlingen (DE)

(72) Inventors: Yuuki Sakaguchi, Fujinomiya (JP); Shinji Ishida, Fujinomiya (JP)

(73) Assignee: Karl Storz SE & Co. KG, Tuttlingen (DE)

( * ) Notice: Subject to any disclaimer, the term of this patent is extended or adjusted under 35 U.S.C. 154(b) by 42 days.

(21) Appl. No.: 14/871,418

(22) Filed: Sep. 30, 2015

(65) Prior Publication Data

US 2016/0015464 A1  Jan. 21, 2016

Related U.S. Application Data

(63) Continuation of application No. PCT/JP2013/059985, filed on Apr. 1, 2013.

(51) Int. Cl.
*A61B 19/00* (2006.01)
*A61B 18/14* (2006.01)
(Continued)

(52) U.S. Cl.
CPC ............ *A61B 19/30* (2013.01); *A61B 17/29* (2013.01); *A61B 18/1445* (2013.01);
(Continued)

(58) Field of Classification Search
CPC ......... A61B 19/30; A61B 90/03; A61B 17/29; A61B 17/61; A61B 2090/034;
(Continued)

(56) References Cited

U.S. PATENT DOCUMENTS

| | | | |
|---|---|---|---|
| 6,402,748 B1 | 6/2002 | Schoenman et al. | |
| 2005/0183656 A1 | 8/2005 | Isaacson et al. | |
| 2007/0175960 A1* | 8/2007 | Shelton, IV | A61B 17/07207 227/178.1 |
| 2008/0029573 A1 | 2/2008 | Shelton et al. | |
| 2008/0244909 A1* | 10/2008 | Golan | A45D 27/29 30/47 |
| 2013/0150860 A1* | 6/2013 | Sidebotham | A61B 17/1666 606/81 |
| 2013/0276598 A1* | 10/2013 | Ivinson | B25B 23/142 81/467 |
| 2013/0331860 A1* | 12/2013 | Komuro | A61B 19/2203 606/130 |

(Continued)

FOREIGN PATENT DOCUMENTS

| | | |
|---|---|---|
| EP | 1813200 A2 | 8/2007 |
| EP | 1884201 A1 | 2/2008 |

(Continued)

OTHER PUBLICATIONS

International Search Report Application No. PCT/JP2013/059985 dated Apr. 25, 2013; Mailing Date: May 14, 2013 2 pages.

(Continued)

*Primary Examiner* — Gary Jackson
*Assistant Examiner* — Zahed Kabir
(74) *Attorney, Agent, or Firm* — Whitmyer IP Group LLC

(57) ABSTRACT

A medical manipulator includes: a manipulator body that has a handle; a drive unit that can be detachably attached to the handle; and an attachment limiting mechanism that is provided to the handle. When the number of times that the drive unit has been attached to and detached from the handle reaches a set number, the attachment limiting mechanism prevents the mounting of the drive unit to the handle. The attachment limiting mechanism has a counting mechanism and a stopper. The counting mechanism counts the number of times that the drive unit is attached and detached. When the count reaches a set number, the stopper is made to protrude into a mounting hole in the handle so as to prevent the insertion of the drive unit into the mounting hole.

8 Claims, 16 Drawing Sheets

(51) Int. Cl.
  *A61B 17/29* (2006.01)
  *A61B 90/00* (2016.01)
  *A61B 17/00* (2006.01)
(52) U.S. Cl.
  CPC ........ *A61B 90/03* (2016.02); *A61B 2017/003* (2013.01); *A61B 2017/0046* (2013.01); *A61B 2017/00199* (2013.01); *A61B 2017/00314* (2013.01); *A61B 2017/00398* (2013.01); *A61B 2017/291* (2013.01); *A61B 2017/2927* (2013.01); *A61B 2090/034* (2016.02); *A61B 2090/0803* (2016.02); *A61B 2090/0814* (2016.02)
(58) Field of Classification Search
  CPC .... A61B 2090/0803; A61B 2090/0814; A61B 2017/00199; A61B 2017/003; A61B 2017/00314; A61B 2017/00398; A61B 2017/0046; A61B 2017/291; A61B 2017/2927

USPC ............................................................ 601/1
See application file for complete search history.

(56)  References Cited

U.S. PATENT DOCUMENTS

2014/0257252 A1\* 9/2014 Ishida .................... A61B 17/29
606/1

FOREIGN PATENT DOCUMENTS

| JP | 2004329624 A | 11/2004 |
| JP | 2008104854 A | 5/2008 |
| WO | 2012124831 A1 | 9/2012 |

OTHER PUBLICATIONS

European Search Report Application No. EP 13 88 1031 dated Jul. 22, 2016; Mailing Date: Aug. 1, 2016 8 pages.

\* cited by examiner

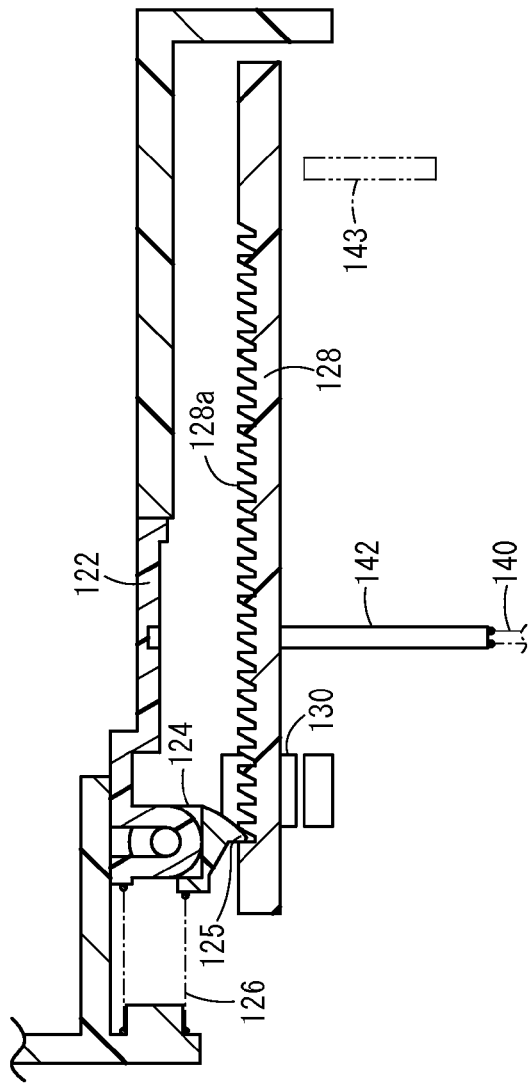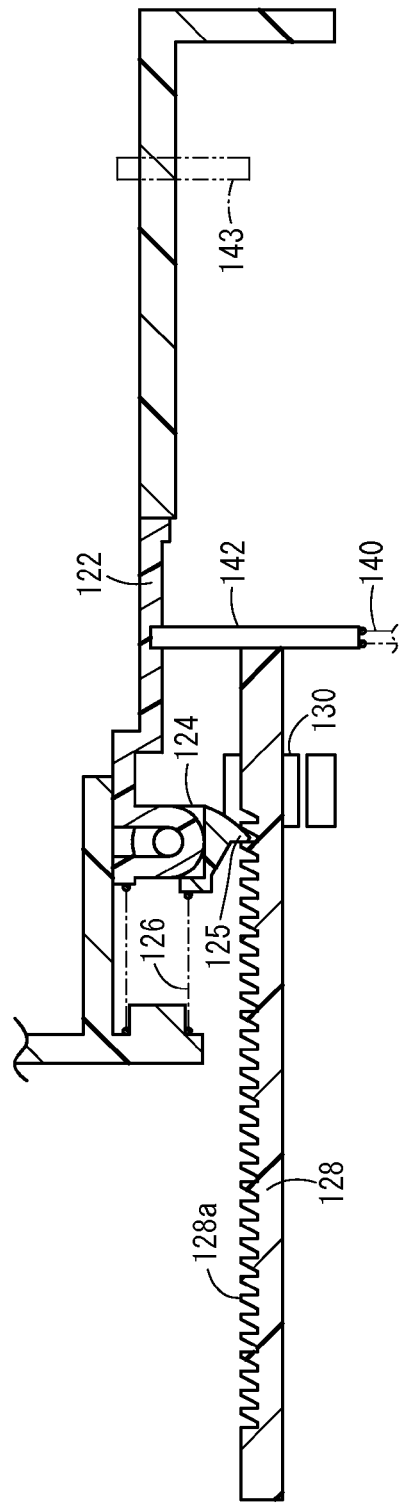
FIG. 14A
FIG. 14B

MEDICAL MANIPULATOR WITH ATTACHMENT LIMITING MECHANISM INCLUDING COUNTING MECHANISM

FIELD OF THE INVENTION

The present invention relates to a medical manipulator equipped with a drive source.

BACKGROUND OF THE INVENTION

In an endoscopic surgical operation (also referred to as "laparoscopic surgery"), one or a plurality of holes are punctured in the abdomen or the like of a patient, and one or more trocars (cylindrical instruments) are inserted through the holes. Thereafter, a laparoscope (camera) and a plurality of forceps are inserted into the body cavity via the one or more trocars. Grippers for gripping biological tissue, scissors, or blades of an electrosurgical scalpel are mounted to the distal end of the forceps as an end effector.

If the laparoscope and the forceps are inserted into the body cavity, an operator operates the forceps while viewing a state of the inner portion of the abdominal cavity, which is shown on a monitor that is connected to the laparoscope. Since the surgical procedure does not require a laparotomy, the burden on the patient is reduced, which reduces the number of days for postoperative recovery and leaving the hospital. For this reason, the fields that such an operative method can be applied to are expected to expand.

Other than typical forceps that are not provided with joints at distal end portions thereof, as forceps that are inserted through a trocar, forceps referred to as a medical manipulator have been developed that are provided with joints at distal end portions and which can carry out a rolling operation or a tilting operation of an end effector (for example, refer to Japanese Patent No. 4391762). In accordance with such a medical manipulator, a high degree of operational freedom is facilitated in the body cavity, manual procedures are made easy, and thus there are a large number of medical cases to which the medical manipulator may be applied.

Further, with the aim of improving operability and facilitating manipulation, a medical manipulator has been proposed that carries out a portion or all of the operations of a distal end working unit by a drive source (motor) (see, for example, Japanese Laid-Open Patent Publication No. 2008-104854). With this type of medical manipulator, a motor serving as a drive source is mounted in a handle on which an operating button is provided. An operating member (a portion corresponding to a forceps) including a shaft and the distal end working unit is capable of being attached and detached with respect to the handle. Multiple types of implements, such as a needle driver, an electrosurgical scalpel, and the like may be used as operating members, and various different types of such operating members are selectively attachable and detachable to and from the handle.

SUMMARY OF THE INVENTION

Incidentally, in the case of a medical manipulator, which is constructed so as to enable a plurality of different operating members to be attached to and detached from a handle in which a drive source is provided, the handle is used in common with respect to a plurality of different end effectors. On the other hand, if the shapes of the handles are different for each type of end effector, an improvement in operability can be expected. However, in the case that differently shaped handles including drive sources are prepared for each of the operating members having different types of end effectors, there is a problem in that the cost of the medical manipulator increases.

To cope with this kind of problem, for example, it may be considered to adopt a configuration in which a common drive unit can be mounted with respect to a manipulator main body (forceps portion) that includes a handle, which is constructed with an appropriate shape corresponding to the type of end effector. On the other hand, in this type of structure, although it is contemplated that a variety of motive power transmitting components (e.g., gears, wires, etc.) are provided, deterioration occurs with use of such power transmitting components. Therefore, it is desirable that the number of times that the manipulator main body is used is subjected to certain limitations.

Taking into consideration the aforementioned problems, the present invention has the object of providing a medical manipulator, in which operability can be improved without a drive source thereof being provided for each of respective handles, together with limiting the number of times that the manipulator main body can be used.

For achieving this object, the medical manipulator of the present invention includes a manipulator main body having a handle, a drive unit that includes a drive source and which is capable of being attached and detached with respect to the handle, and a number of times limiting mechanism disposed on the handle, which, in the event that the number of times that the drive unit has been attached and detached with respect to the handle has reached a predetermined number of times, prevents attachment of the drive unit with respect to the handle.

According to the above configuration, if the number of times that the drive unit has been attached and detached with respect to the handle reaches a predetermined number of times (number of times usage limit), by an action of the number of times limiting mechanism, it becomes impossible for the drive unit to be attached to the handle. Stated otherwise, use of the manipulator main body in excess of the number of times usage limit can be forcibly restricted. Further, because the drive unit including the drive source is capable of attachment and detachment with respect to the handle, there is no need for a drive source to be provided for each of handles having different shapes and functions. More specifically, in the medical manipulator of the present invention, a common drive unit can be mounted and used with respect to the handle, which is constructed with an appropriate shape corresponding to the type of end effector. Accordingly, without a steep rise in cost, suitable operability can be obtained.

The number of times limiting mechanism may include an operating body that is mechanically interlinked with attachment and detachment of the drive unit with respect to the handle, and a counter mechanism that is operated by a predetermined amount with each time of operation of the operating body. Further, when the counter mechanism has been operated a predetermined number of times from an initial state thereof, attachment of the drive unit with respect to the handle may be prevented.

In accordance with the above configuration, by providing the counter mechanism and the operating body that is interlinked mechanically with attachment and detachment of the drive unit, the number of times of attachment and detachment is reliably counted, and therefore, when the predetermined number of times is reached, it is possible for the attachment prevention function to be triggered reliably.

The number of times limiting mechanism may include a stopper that is changed to a regulating condition when the counter mechanism has been operated a predetermined number of times from the initial state thereof, and the stopper, in the regulating condition, may project into a movement path of the drive unit when the drive unit is attached to the handle.

According to the above structure, even if it is attempted to attach the drive unit to the handle when the stopper is in the regulating condition, since the drive unit becomes caught on or engaged with the stopper, attachment of the drive unit can physically be prevented. Consequently, use of the manipulator main body in excess of the number of times usage limit can reliably be prevented.

The number of times limiting mechanism may include a lock member that is displaced to a regulating position when the counter mechanism has been operated a predetermined number of times from the initial state thereof, and the lock member, in the regulating position, may prevent movement of the operating body.

According to the above structure, in a state in which the lock member has arrived at the regulating position, even if it is attempted to attach the drive unit, since movement of the operating body is prevented, attachment of the drive unit can physically be prevented. Consequently, use of the manipulator main body in excess of the number of times usage limit can reliably be prevented.

The operating body may include a slider, which is pressed by the drive unit and is displaced from a first position to a second position accompanying attachment of the drive unit with respect to the handle, and is returned from the second position to the first position accompanying removal of the drive unit from the handle.

In accordance with the above configuration, an operating body constituted as a slider can be advanced and retracted accompanying attachment and detachment of the drive unit with respect to the handle. Consequently, attachment and detachment of the drive unit can be reliably detected mechanically, and the counter mechanism can be operated.

An operating body biasing means may further be included for biasing the operating body toward the first position.

According to the above configuration, when the drive unit is removed from the handle, the operating body can be restored reliably to the first position. Consequently, with each attachment and detachment of the drive unit, the counter mechanism can reliably be operated by a predetermined amount.

The number of times limiting mechanism may be capable of being operated from a non-regulating condition to a regulating condition, and may include a stopper that, in the regulating condition, projects into a movement path of the drive unit when the drive unit is attached to the handle. The counter mechanism may include an intermediate transmission mechanism that is driven accompanying operation of the operating body, and a rotating body that is rotated by the intermediate transmission mechanism. Further, in a state in which the number of times of attachment and detachment is less than the predetermined number of times, the rotating body may engage with the stopper to maintain the non-regulating condition, and in a state in which the number of times of attachment and detachment has reached the predetermined number of times, the rotating body may allow the stopper to be changed to the regulating condition.

With the above configuration, movements of the operating body, which is operated by attachment and detachment of the drive unit, are transmitted to the rotating body through the intermediate transmission mechanism. When the number of attachments and detachments reaches the predetermined number of times, the regulating condition is brought about in which the stopper projects into the movement path of the drive unit. In this condition, even if it is attempted to attach the drive unit to the handle, since the drive unit becomes caught on or engaged with the stopper, attachment of the drive unit can physically be prevented. Consequently, use of the manipulator main body in excess of the number of times usage limit can reliably be prevented.

Each of the operating body, the intermediate transmission mechanism, and the rotating body may be constituted from a plate-shaped member, and the stopper may be changed from the non-regulating condition to the regulating condition accompanying a tilting movement of the stopper from an initial posture.

According to the above structure, the number of times limiting mechanism can be given a thin profile, and the installation volume within the handle can be reduced. Consequently, an increase in scale of the handle together with arrangement of the number of times limiting mechanism therein can be suppressed.

The intermediate transmission mechanism may include a plurality of mutually intermeshed gears.

According to the above configuration, the amount of rotation of the rotating body, corresponding to the displacement amount of the operating body at the time of attachment and detachment of the drive unit with respect to the handle, can be adjusted by the gear ratio of the gears. Therefore, by adjusting the gear ratio, the predetermined number of times to trigger the attachment prevention function can easily be set.

The number of times limiting mechanism may include a stopper biasing member that biases the stopper toward the regulating condition, and a notch may be provided in the rotating body. In a state in which the number of times of attachment and detachment is less than the predetermined number of times, an abutment provided on the stopper may abut against the rotating body, whereby the stopper is retained in the non-regulating condition in opposition to a biasing force of the stopper biasing member. Further, in a state in which the number of times of attachment and detachment has reached the predetermined number of times, the abutment provided on the stopper may be capable of entering into the notch.

According to the above configuration, the stopper is not operated in a state in which the number of times of attachment and detachment is less than the predetermined number of times, whereas the stopper can reliably be operated when the predetermined number of times is reached.

BRIEF DESCRIPTION OF THE DRAWINGS

FIG. 14A is a schematic cross-sectional view showing a structural example in which a lock member is provided in the number of times limiting mechanism according to a modification;

FIG. 14B is a schematic perspective view showing a condition in which the lock member is triggered in the number of times limiting mechanism according to the modification.

DETAILED DESCRIPTION OF THE INVENTION

Hereinafter, a preferred embodiment of a medical manipulator according to the present invention will be described in detail below with reference to the accompanying drawings.

Figure 1:
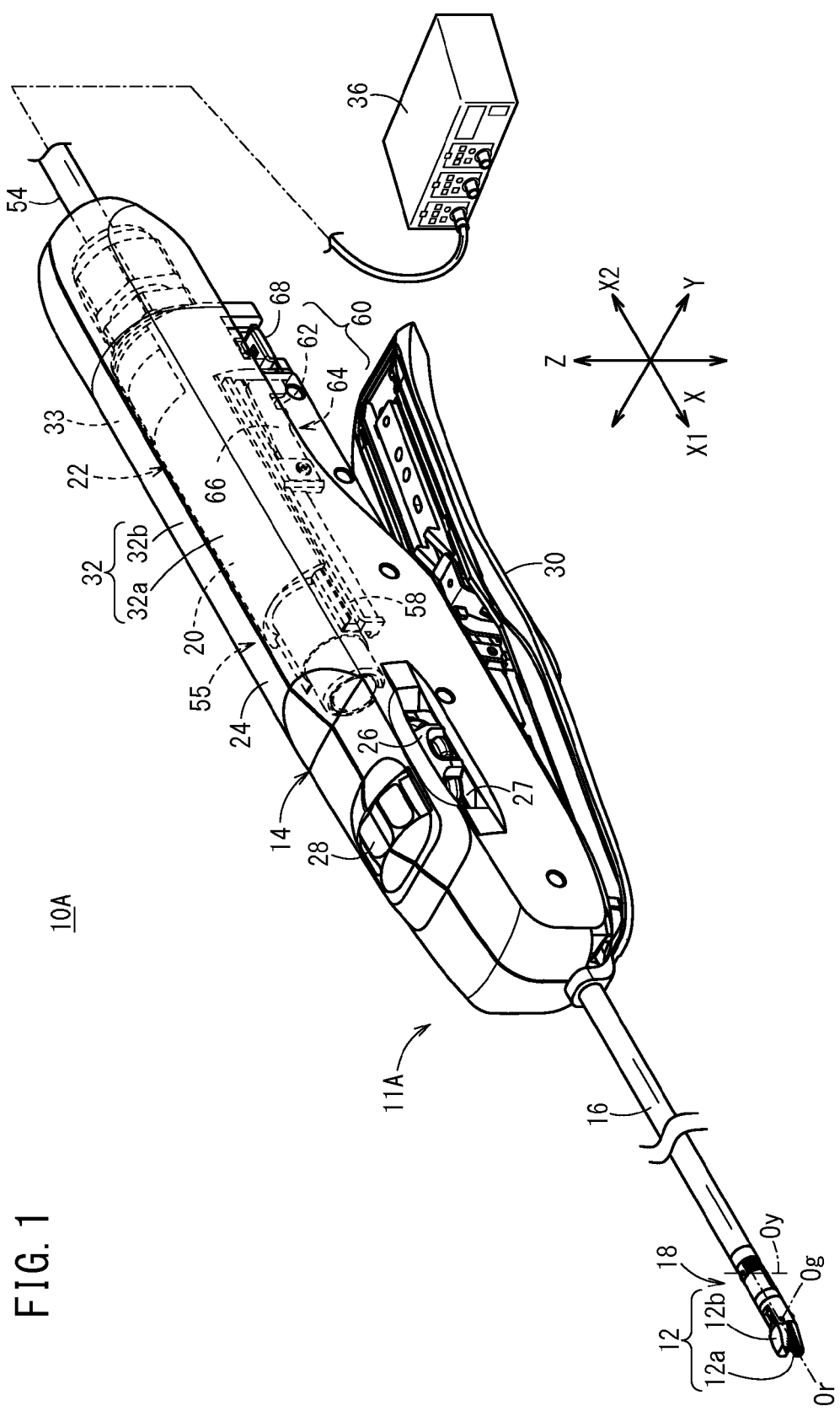
FIG. 1 is a perspective view with partial omission of a medical manipulator according to an embodiment of the present invention.

FIG. 1 is a perspective view with partial omission of a medical manipulator 10A (hereinafter referred to in abbreviated form as a "manipulator 10A") according to an embodiment of the present invention. The manipulator 10A is a medical device that grasps a needle, a thread, or a part of the living body or touches the living body using a gripper 12 (end effector) provided at the distal end thereof, and carries out a predetermined treatment.

The manipulator 10A comprises a handle 14 on which a plurality of input operating members are provided, a shaft 16 that extends from the handle 14, a distal end working unit 18 disposed on a distal end of the shaft 16 including a gripper 12, and a drive unit 22 in which a motor 20 (drive source) is provided for driving the distal end working unit 18, and which is capable of attachment and detachment to and from the handle 14. A manipulator main body 11A is made up from the handle 14, the shaft 16, and the distal end working unit 18.

In the following description, in relation to the manipulator 10A and the constituent elements thereof, in the drawings, the X direction indicates a forward and rearward longitudinal direction, the Y direction indicates a left and right lateral direction, and the Z direction indicates an up and down vertical direction. In particular, the X1 direction is a forward direction, and the X2 direction is a rearward direction.

With the manipulator 10A according to the present embodiment, the manipulator main body 11A and the drive unit 22 can be attached and detached to and from each other. In a state in which the drive unit 22 is taken out from the manipulator main body 11A (see FIG. 2), the driving force from the motor 20 is not transmitted to the distal end working unit 18. On the other hand, in a state in which the drive unit 22 is mounted on the handle 14, when the motor 20 is driven, the driving force of the motor 20 is transmitted to the distal end working unit 18.

The manipulator 10A shown in FIG. 1 is constituted as a needle driver that is capable of grasping a medical needle (a curved needle or the like) with the gripper 12 disposed on the distal end thereof. The gripper 12 is a portion that carries out a surgical treatment, and in the illustrated example, the gripper 12 includes first and second gripper members 12a, 12b, and is configured to carry out opening and closing operations on the basis of a predetermined opening and closing operation axis Og. In the illustrated example, although concerning the gripper 12, a case has been described in which the first gripper member 12a is constituted as a fixed member and the second gripper member 12b is constituted as a movable member, both of the gripper members 12a, 12b may be constituted as movable members.

The posture of the distal end working unit 18 including the gripper 12 can be changed at a plurality of degrees of freedom with respect to the shaft 16. In the present embodiment, the distal end working unit 18 can carry out a "tilting operation" (swinging operation) in which the distal end working unit 18 is operated to tilt in left and right (transverse or lateral) directions with respect to an axis of the shaft 16 about a tilt axis Oy, and a "rolling operation" in which the distal end working unit 18 is rotated about the axial line (roll axis Or) in the longitudinal direction of the distal end working unit 18. The tilt axis Oy is not limited to being set in the vertical direction, and the tilt axis Oy may be set in a different direction that intersects the axis of the shaft 16.

The shaft 16 is an oblong small diameter tubular member that connects the handle 14 and the distal end working unit 18. In FIG. 1, a portion of the shaft 16 is omitted from illustration, and the shaft 16 is rendered shorter than it actually is. A plurality of members configured to make up a power transmission mechanism are inserted through and arranged in a hollow portion of the shaft 16. Such a power transmission mechanism transmits, from the handle 14 to the distal end working unit 18, power that is necessary for carrying out the opening and closing operation of the gripper 12, and the rolling operation and the tilting operation of the distal end working unit 18.

A structure may be provided in which one or a plurality of joints are provided at an intermediate location in the longitudinal direction of the shaft 16 to enable the tilting operation by the joints. Further, a structure may be provided in which the rolling operation is enabled at the proximal end of the shaft 16, or at an intermediate location in the longitudinal direction of the shaft 16.

The handle 14 is a portion that is gripped by an operator during use of the manipulator 10A, and by input operating members (in the present embodiment, a later described tilt wheel 26, a rolling switch 28, and a lever 30) being touched and operated by a finger, drives the distal end working unit 18 that is connected to the distal end of the shaft 16.

The handle 14 comprises a body portion 24 that is connected to a proximal end of the shaft 16, the tilt wheel 26 constituting a tilt operating unit that is provided on the body portion 24, the rolling switch 28 constituting a rolling operating unit that is provided on the body portion 24, and the lever 30 constituting an opening and closing operating unit that is provided on the body portion 24.

The body portion 24 makes up a part that is gripped by a user when the manipulator 10A is used. In the present embodiment, the body portion 24 is constituted in the form of a stick that extends over a certain length in the axial direction of the shaft 16. The body portion 24 includes a casing 32 made up from a left cover 32a and a right cover 32b, with frames, drive components (pulleys, gears, wires, etc.) or the like being arranged in the interior of the casing 32. For insertion and installation of the drive unit 22 in the interior of the casing 32 from the rear side, a rearwardly open installation hole 33 is formed.

The tilt wheel 26 for carrying out a tilting operation of the distal end working unit 18 is disposed near the center in the longitudinal direction of the body portion 24, and is rotatable about the vertically oriented axis of the handle 14. The tilt wheel 26 is constituted as a manual operating member, and the tilt wheel 26 partially protrudes from openings 27 provided on left and right sides of the casing 32.

When the tilt wheel 26 is operated by being rotated, the operating force applied thereto is transmitted mechanically to the distal end working unit 18 through a tilting operation power transmission system, which is disposed internally in the handle 14 and the shaft 16, whereupon the distal end working unit 18 is tilted about an axis (tilt axis Oy) in a non-parallel direction with respect to the axis of the shaft 16. More specifically, when the tilt wheel 26 is rotated clockwise as viewed in plan, the distal end working unit 18 is tilted in a rightward direction about the handle 14, whereas when the tilt wheel 26 is rotated counterclockwise as viewed in plan, the distal end working unit 18 is tilted in a leftward direction about the handle 14.

With the manipulator 10A of the illustrated example, the rolling switch 28 for carrying out a rolling operation of the distal end working unit 18 is disposed on an upper portion in the vicinity of the distal end of the body portion 24. In the present embodiment, the rolling switch 28 is constituted as an electrical manipulating portion, which supplies an operating command to the motor 20 through a controller 36.

In a state in which the drive unit 22 is mounted in the handle 14, and the power source of the controller 36 is turned on, when the rolling switch 28 is operated and moved, the operating state (position) of the rolling switch 28 is detected by the controller 36, the motor 20 is driven under a controlling action of the controller 36, and by the driving force of the motor 20 being transmitted to the distal end working unit 18, the distal end working unit 18 is rotated about the longitudinal axis (roll axis Or) of the distal end working unit 18.

A lever 30 for performing an opening and closing operation of the gripper 12 is disposed on a lower part of the body portion 24, and is mounted so that the lever 30 swings upward and downward about the distal end side thereof, which serves as a support point. According to the present embodiment, the lever 30 is constructed as a manual operating member, in which an opening and closing operation of the gripper 12 is carried out by mechanically transmitting to the gripper 12 of the distal end working unit 18 an operating force applied with respect to the lever 30. More specifically, a structure is provided in which the gripper 12 is opened when the lever 30 is opened, and the gripper 12 is closed when the lever 30 is closed.

As shown in FIG. 1, the drive unit 22 of the manipulator 10A is used in a condition of being connected to the controller 36 through a cable 54. The controller 36 controls the supply of power and driving or the like of the motor 20, and receives electrical power from an external power source. In a state in which the drive unit 22 is mounted on the handle 14, when the rolling switch 28 is operated, the controller 36 controls driving of the motor 20 in response to operation thereof. The rotation of the motor 20 may be detected, and the motor 20 may be feedback controlled through the controller 36.

The form of use can be one in which, concerning the manipulator 10A that is constructed in the foregoing manner, the manipulator main body 11A can be discarded after being used a predetermined number of times, whereas the drive unit 22 can be used repeatedly many times by changing the manipulator main body 11A that is connected to the drive unit 22.

Figure 3:
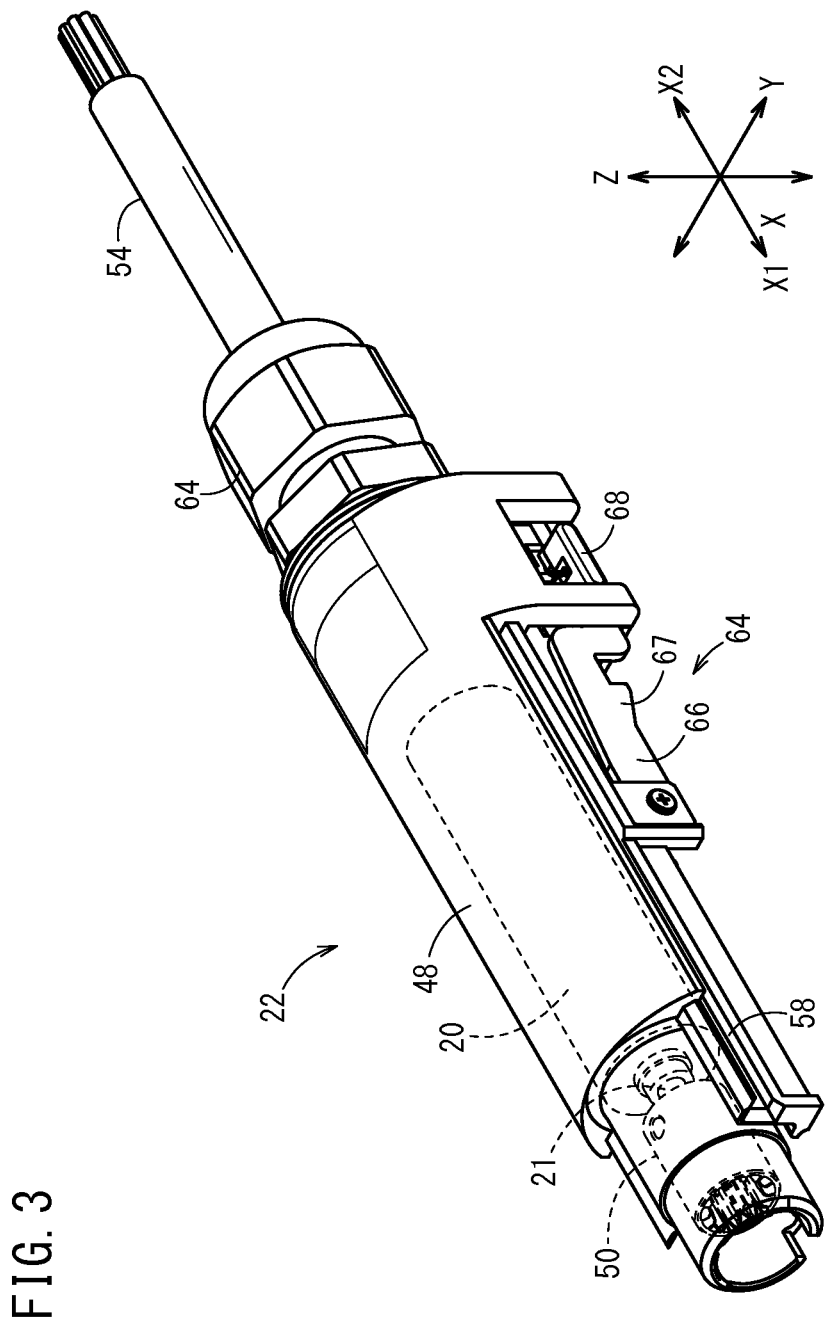
FIG. 3 is a perspective view of a drive unit of the medical manipulator illustrated in FIG. 1.

FIG. 3 is a perspective view of the drive unit 22. The drive unit 22 includes a housing 48, a motor 20 (drive source) disposed inside the housing 48, and a drive coupling 50 (drive member) that is fixed to the output shaft 21 of the motor 20. A cable 54 including power lines and signal lines is connected to the proximal end side of the drive unit 22.

In a state in which the drive unit 22 is attached to the handle 14 (see FIG. 1), the drive coupling 50, which is fixed to the output shaft 21 of the motor 20, is fitted (enmeshed) with a non-illustrated driven coupling (driven member) disposed on the side of the handle 14. In the state with the drive coupling 50 and the driven coupling fitted together, when the motor 20 is rotated, the rotary driving force of the motor 20 is transmitted to the side of the handle 14 through the drive coupling 50 and the driven coupling.

Figure 2:
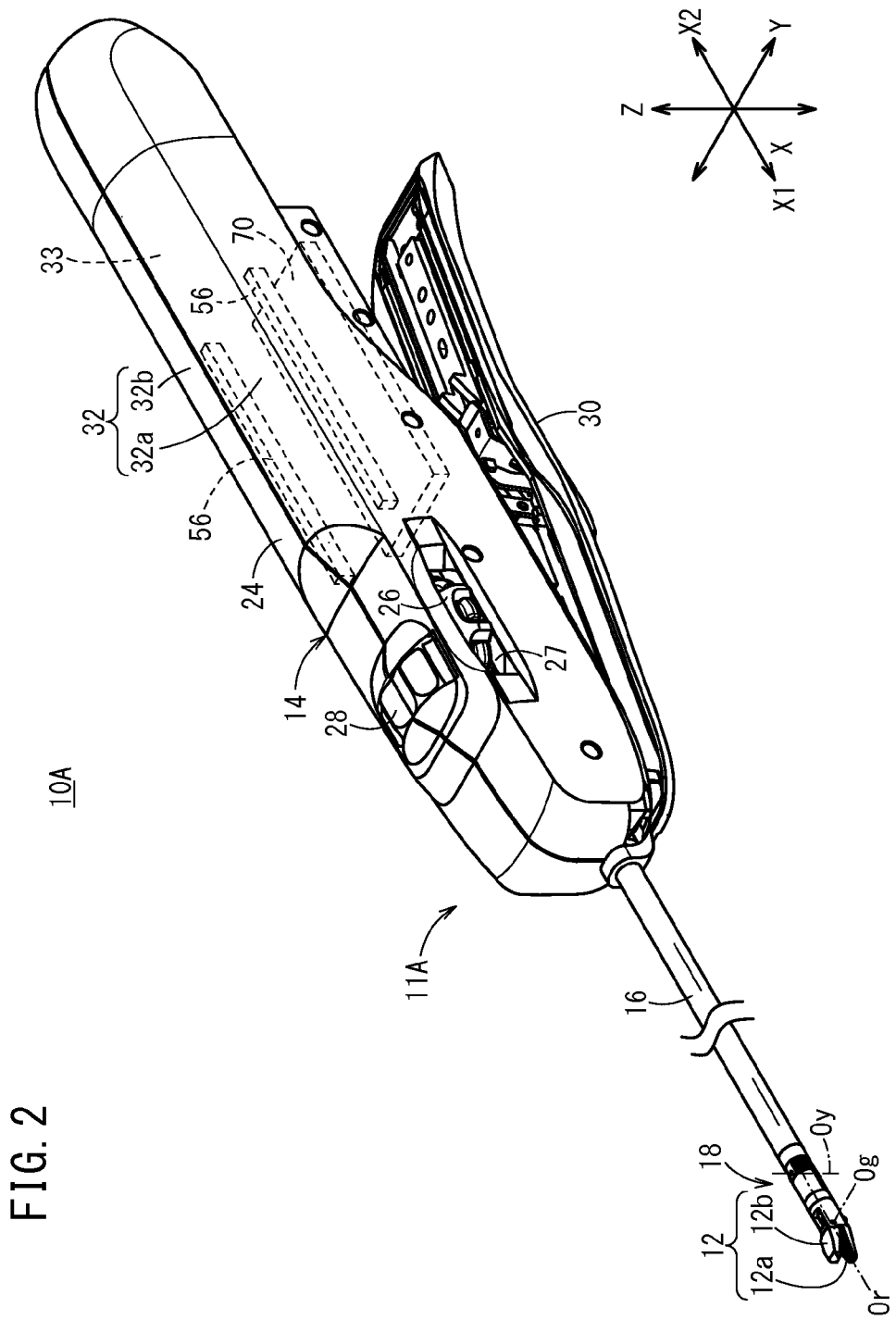
FIG. 2 is a perspective view with partial omission of a manipulator main body in the medical manipulator shown in FIG. 1.

As shown in FIG. 2, guide rails 56 that extend along a longitudinal (forward and rearward) direction of the handle 14, are provided on the handle 14. As illustrated, the guide rails 56 are disposed on both left and right side of an inner surface of the casing 32. As shown in FIG. 3, groove-shaped guide receiving members 58 that extend in the longitudinal direction of the drive unit 22 are disposed on side surfaces on both left and right sides of the housing 48.

A guide mechanism 55 (see FIG. 1) is constituted by the guide rails 56 and the guide receiving members 58. When the drive unit 22 is attached with respect to the handle 14, under an action of the guide mechanism 55, the drive unit 22 can be moved smoothly relative to the handle 14. Consequently, the drive unit 22 can be mounted easily and reliably at an accurate positional relationship with respect to the handle 14.

Although omitted from illustration in FIGS. 1 and 2, handle-side terminals are provided on the handle 14. Further, although illustration thereof is omitted in FIG. 3, unit-side terminals are provided on the drive unit 22. In a state in which the drive unit 22 is attached to the handle 14, the handle-side terminals and the unit-side terminals are placed in contact. According to this structure, the operating state of the rolling switch 28 can be detected by the controller 36, and the controller 36 can appropriately control driving of the motor 20.

As shown in FIG. 1, in the drive unit 22, a lock mechanism 60 is provided that restricts the drive unit 22 so as not to become detached from the handle 14, in a state in which the drive unit 22 has been attached to the handle 14. The lock mechanism 60 of FIG. 1 includes an engagement member 62 disposed on the handle 14, and a lever device 64 disposed on the drive unit 22.

As shown in FIG. 3, the lever device 64 includes the lever member 66, an operating tab 68, and a lever biasing member (not shown). An engagement pawl 67 is provided on the lever member 66 which is swingable with respect to the housing 48. The operating tab 68 is disposed on a proximal end of the lever member 66. The lever biasing member biases the lever member 66 elastically in a direction in which the engagement pawl 67 projects (a downward direction in the case of the illustrated example).

Accompanying attachment of the drive unit 22 to the handle 14, the engagement pawl 67 disposed on the lever member 66 engages with the engagement member 62 disposed in the handle 14, whereby the drive unit 22 is prevented from becoming detached and separating away from the handle 14. On the other hand, by releasing the engagement between the engagement member 62 and the engagement pawl 67 of the lever member 66, the drive unit 22 is capable of being detached from the handle 14.

Figure 4:
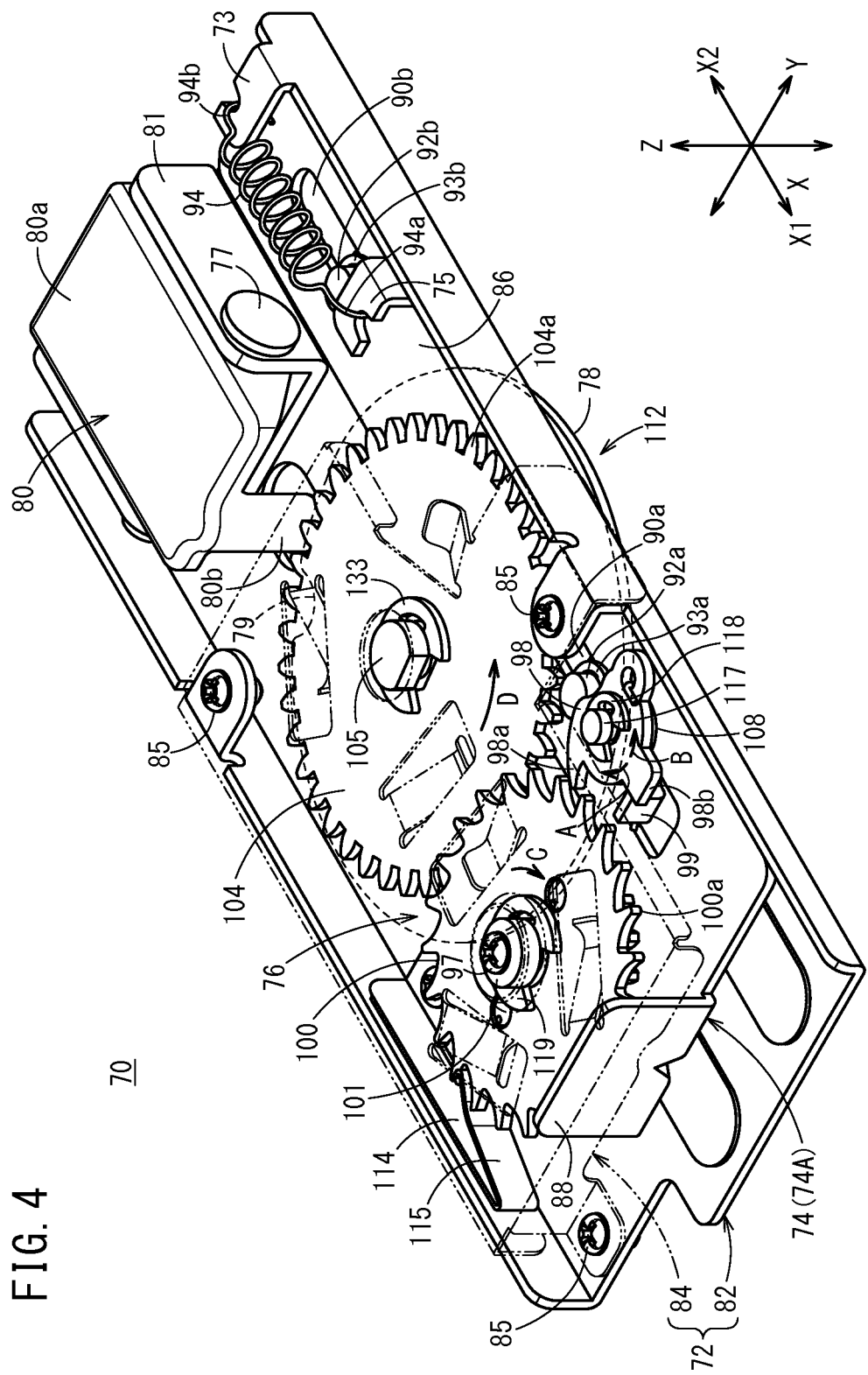
FIG. 4 is a perspective view of a number of times limiting mechanism.

As shown in FIG. 2, a number of times limiting mechanism 70 is further provided in the handle 14. The number of times limiting mechanism 70 serves to prevent attachment of the drive unit 22 with respect to the handle 14, in the event that the number of times of attachment and detachment of the drive unit 22 with respect to the handle 14 has reached a predetermined number of times. The preset number of times is a number of times that the manipulator main body 11A is used. According to the present invention, a case in which the drive unit 22 has been attached and detached one time with respect to the manipulator main body 11A is regarded as one usage of the manipulator main body 11A. The number of times at which attachment of the drive unit 22 is prevented may be set arbitrarily. However, the number of times typically is set, for example, to a range of from 10 times to fifty times. FIG. 4 is a perspective view of the number of times limiting mechanism 70 according to one structural example thereof, and FIG. 5 is an exploded perspective view of the number of times limiting mechanism 70.

Figure 5:
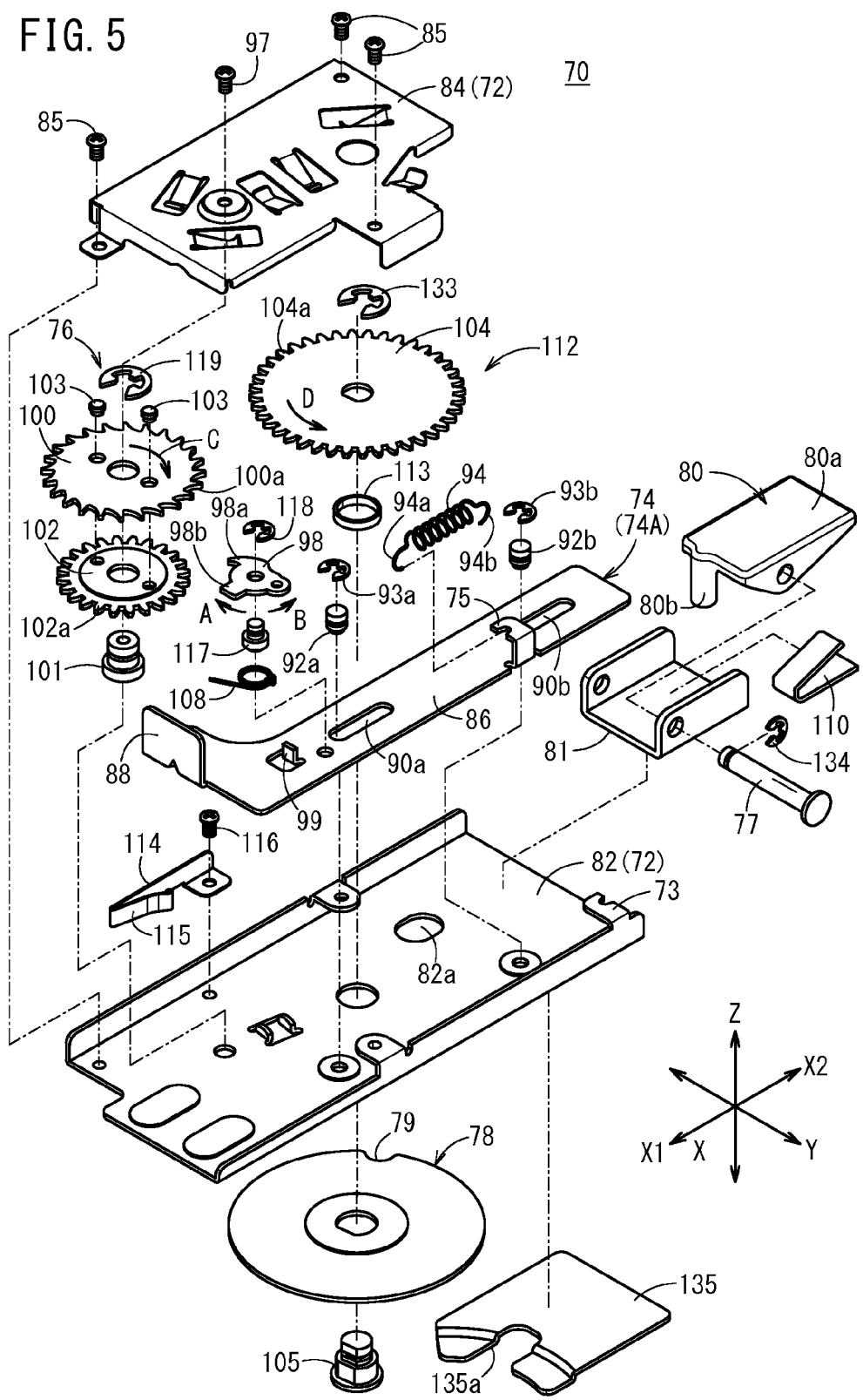
FIG. 5 is an exploded perspective view of the number of times limiting mechanism.

As shown in FIGS. 4 and 5, the number of times limiting mechanism 70 includes a frame 72, an operating body 74 that is capable of sliding in forward and rearward directions with respect to the frame 72, an intermediate transmission mechanism 76 linked operatively with the operating body 74, a rotating body 78 that is rotated by the intermediate transmission mechanism 76, and a stopper 80 that can be varied between a non-regulating condition and a regulating condition, and which prevents attachment of the drive unit 22 to the handle 14 in the regulating condition.

The frame 72 includes a frame main body 82, and a covering body 84 that is fixed to the frame main body 82. The frame 72 is fixed in a predetermined position in the interior of the handle 14. The frame main body 82 of the present illustrated example is substantially rectangular as viewed in plan. The operating body 74, the intermediate transmission mechanism 76, the rotating body 78, and the stopper 80 are disposed on the frame 72. The covering body 84 is fixed by a suitable fixing means 85 (e.g., screws in the illustrated example) with respect to the frame main body 82. The frame main body 82 and the covering body 84 can be fabricated, for example, by sheet metal processing. The frame main body 82 and the covering body 84 may also be constituted from a resin.

The operating body 74 is interlinked mechanically with attachment and detachment of the drive unit 22 with respect to the handle 14. More specifically, accompanying attachment of the drive unit 22 with respect to the handle 14, the operating body 74 is pressed by the drive unit 22, and is displaced from a retracted position (first position) to an advanced position (second position). Further, accompanying removal of the drive unit 22 from the handle 14, the operating body 74 returns from the advanced position to the retracted position. FIG. 4 shows the operating body 74 in the retracted position. In this manner, the operating body 74 in the present illustrated example is constituted as a slider 74A that can be advanced and retracted accompanying attachment and detachment of the drive unit 22 with respect to the handle 14.

The operating body 74 includes a flat base member 86 that contacts the frame main body 82 and is capable of sliding along the frame main body 82, and a pressed member 88 that projects out from the base member 86. On the base member 86, a plurality of (two in the illustrated example) elongate guide holes 90a, 90b, which extend in the longitudinal direction, are disposed at a given interval in the longitudinal direction. Guide pins 92a, 92b are fixed to the frame main body 82, and the guide pins 92a, 92b are inserted into the guide holes 90a, 90b. By attachment of latching parts 93a, 93b (C clips in the illustrated example) to the guide pins 92a, 92b, the guide pins 92a, 92b are prevented from being pulled out from the guide holes 90a, 90b. Under a guiding action due to engagement between the guide holes 90a, 90b and the guide pins 92a, 92b, the operating body 74 is capable of sliding stably with respect to the frame 72 in the longitudinal direction (X direction).

The pressed member 88 is a portion that is pressed by the drive unit 22 accompanying movement of the drive unit 22 when the drive unit 22 is attached with respect to the handle 14. In the illustrated example, the pressed member 88 is bent and is disposed so as to project upwardly at the distal end of the base member 86. The pressed member 88 may be disposed integrally with respect to the base member 86, or may be a member that is attached to the base member 86.

The operating body 74 is biased elastically toward the retracted position by the return spring 94 (operating body biasing means). In the present illustrated example, one end 94a of the return spring 94 is engaged with a hooking piece 75 disposed on the operating body 74, and another end 94b of the return spring 94 is engaged with a hooking piece 73 disposed on the frame 72. By an elastic action that acts to shrink, the return spring 94 biases the operating body 74 in a rearward direction (X2 direction) with respect to the frame 72. Alternatively, by an elastic action that acts to expand, the return spring 94 may bias the operating body 74 in a rearward direction with respect to the frame 72.

The intermediate transmission mechanism 76 includes a pawl member 98 displaced together with the operating body 74, a ratchet wheel 100 that is driven by the pawl member 98, a first gear 102 that is connected to the ratchet wheel 100, and a second gear 104 that is enmeshed with the first gear 102.

The pawl member 98 is plate-shaped, and is pivotally supported by a shaft 117 that is fixed to the base member 86, so that the pawl member 98 is rotatable (swingable) within a predetermined angular range about the shaft 117 with respect to the operating body 74. By attachment of a latching part 118 (a C clip in the illustrated example) to the shaft 117, the pawl member 98 is prevented from being pulled off from the shaft 117. An engagement pawl 98a, which is capable of engaging with the ratchet wheel 100, and an abutting projection 98b, which is capable of abutting against a latching piece 99 disposed on the base member 86, are provided on the pawl member 98.

The pawl member 98 is elastically biased by a pawl biasing member 108 in the A direction shown in FIG. 5. The pawl biasing member 108 is in the form of a torsion spring. However, the pawl biasing member 108 may be of another form such as a coil spring or the like, or alternatively, may be constituted from an elastic member other than a spring. By abutment between the latching piece 99 and the abutting projection 98b, the pawl member 98 is prevented from being rotated further in the A direction. On the other hand, if the pawl member 98 receives a force equal to or greater than a predetermined amount in the B direction that is opposite to the A direction, the pawl member 98 can be rotated in the B direction in opposition to the elastic force of the pawl biasing member 108.

The ratchet wheel 100 is disposed rotatably through a shaft 101 with respect to the frame 72. The ratchet wheel 100 of the present illustrated example is constituted by a comparatively thin flat plate. By attachment of a latching part 119 (a C clip in the illustrated example) to the shaft 101, the ratchet wheel 100 and the first gear 102 are prevented from being pulled off from the shaft 101. The shaft 101 is fixed to the covering body 84 by a fixing part 97 (a screw in the illustrated example).

Teeth 100a, which are disposed on the outer circumference of the ratchet wheel 100, are capable of engaging with the engagement pawl 98a of the pawl member 98. A latch member 114 provided on the frame main body 82 also engages with the teeth 100a of the ratchet wheel 100. The latch member 114 is fixed to the frame main body 82 by a fixing means 116 (a screw in the illustrated example). A latch piece 115, which is displaceable elastically, is provided on the latch member 114. The latch piece 115 permits the ratchet wheel 100 to be operated in the C direction, but engages with the teeth 100a of the ratchet wheel 100 in order to prevent the ratchet wheel 100 from rotating in the direction opposite to the C direction. Stated otherwise, the ratchet wheel 100 is capable of rotating only in the C direction.

The first gear 102 and the ratchet wheel 100 are arranged coaxially. The first gear 102 of the present illustrated example is constituted by a comparatively thin flat plate. The ratchet wheel 100 and the first gear 102 are fixed together mutually so as to be incapable of rotating relative to each other. In the present illustrated example, two retaining pins 103 are inserted into and engage both with the ratchet wheel 100 and the first gear 102, whereby the ratchet wheel 100 and the first gear 102 are incapable of relative rotation. The first gear 102 and the ratchet wheel 100 rotate together integrally. Consequently, in the same manner as the ratchet wheel 100, the first gear 102 is capable of rotating only in the C direction.

The second gear 104 is disposed rotatably through a shaft 105 with respect to the frame 72. The second gear 104 of the present illustrated example is constituted by a comparatively thin flat plate. By attachment of a latching part 133 (a C clip in the illustrated example) to the shaft 105, the second gear 104 is prevented from being pulled off from the shaft 105. Teeth 102a, which are disposed on the outer circumference of the first gear 102, and teeth 104a, which are disposed on the outer circumference of the second gear 104, are enmeshed. Consequently, accompanying rotation of the first gear 102 in the C direction, the second gear 104 is rotated in the D direction about the shaft 105. A ring-shaped spacer 113 is arranged between the second gear 104 and the frame main body 82.

The rotating body 78 is arranged coaxially with the second gear 104, and in the illustrated example, is disposed on a lower side surface of the frame main body 82. The rotating body 78 of the present illustrated example is constituted by a comparatively thin flat plate. The second gear 104 and the rotating body 78 are fixed together mutually via the shaft 105 so as to be incapable of rotating relative to each other, and the rotating body 78 and the second gear 104 rotate together integrally. The rotating body 78 is disk-shaped with a diameter greater than that of the second gear 104. A notch 79 is provided at one portion in the circumferential direction on the outer circumference thereof.

According to the present embodiment, a counter mechanism 112, which is operated by a predetermined amount with each operation of the operating body 74, is constituted by the aforementioned ratchet wheel 100, the first gear 102, the second gear 104, and the rotating body 78.

From a non-regulating condition in which attachment of the drive unit 22 with respect to the handle 14 is permitted (see FIG. 4), the stopper 80 can be operated to assume a regulating condition (see FIG. 7) in which attachment of the drive unit 22 to the handle 14 is prevented. The stopper 80 of the present illustrated example is supported rotatably by a shaft 77, which is inserted through a stopper support member 81 that is fixed to the frame 72 (frame main body 82). By attachment of a latching part 134 (a C clip in the illustrated example) to the shaft 77, the shaft 77 is prevented from being pulled off from the stopper support member 81.

A condition in which the stopper 80 lies substantially parallel with respect to the frame main body 82 is referred to as a "non-regulating condition", and a condition in which the stopper 80 is raised at a certain angle of inclination with respect to the frame main body 82 is referred to as a "regulating condition". In the regulating condition, the stopper 80 projects into the movement path (inside the installation hole 33) of the drive unit 22 when the drive unit 22 is attached to the handle 14.

An abutment 80b, which is capable of engaging with the rotating body 78, is disposed on the stopper 80. The abutment 80b of the present illustrated example projects downward from a distal end side of the stopper 80, and is inserted through a hole 82a in the frame main body 82. The stopper 80 is biased elastically at all times in the direction of the regulating condition by a stopper biasing member 110. The stopper biasing member 110 of the illustrated example is constituted as a plate spring, which is arranged between the stopper 80 and the stopper support member 81. However, the stopper biasing member 110 may be of another form such as a coil spring or the like, or alternatively, may be constituted from an elastic member other than a spring.

As will be discussed later, in a state in which the number of times that the drive unit 22 has been attached and detached with respect to the handle 14 is less than a predetermined number of times, the outer circumference (an outer circumferential portion where the notch 79 is not disposed) of the rotating body 78 is in a position that faces the abutment 80b, and the abutment 80b abuts against the rotating body 78. Therefore, the stopper 80 is retained in the non-regulating condition in opposition to the elastic force (biasing force) of the stopper biasing member 110. On the other hand, in a state in which the number of times of attachment and detachment has reached the predetermined number of times, the abutment 80b becomes aligned with the position (phase) of the notch 79 of the rotating body 78, whereby the stopper 80 becomes tilted accompanying entry of the abutment 80b into the notch 79, and a change to the regulating condition takes place.

A stay member 135 is fixed to a lower portion of the frame main body 82. The stay member 135 is a member that supports from below a region within the rotating body 78 that is pressed by the abutment 80b. As a result of the rotating body 78 being supported from below by the stay member 135, even in a condition in which the abutment 80b presses on the rotating body 78, the rotating body 78 is not tilted. A notch 135a that allows entry of the abutment 80b therein is provided on the stay member 135. The notch 135a is disposed at a position across from the hole 82a of the frame main body 82. Consequently, when the notch 79 of the rotating body 78 arrives at the position of the abutment 80b, there is no hindrance to the stopper 80 changing from the non-regulating condition to the regulating condition.

The manipulator 10A according to the present embodiment is constructed basically as described above. Next operations and advantages of the manipulator 10A will be described.

In a state in which the drive unit 22 has not been attached and detached even one time with respect to the manipulator main body 11A, or in other words, in an unused state of the manipulator main body 11A, the number of times limiting mechanism 70 is in an initial state, as shown in FIG. 4. In the initial state of the number of times limiting mechanism 70, the notch 79 provided on the rotating body 78 is in a position shifted in a reverse direction to the direction of rotation (D direction) of the rotating body 78 from the abutment 80b of the stopper 80, by a portion corresponding to the predetermined number of times (number of times usage limit). Therefore, the abutment 80b is stopped by the rotating body 78, and a fallen state of the stopper 80, i.e., the non-regulated condition, is retained. Further, at this time, the operating body 74 is retained in the retracted position by the elastic force of the return spring 94.

Figure 6:
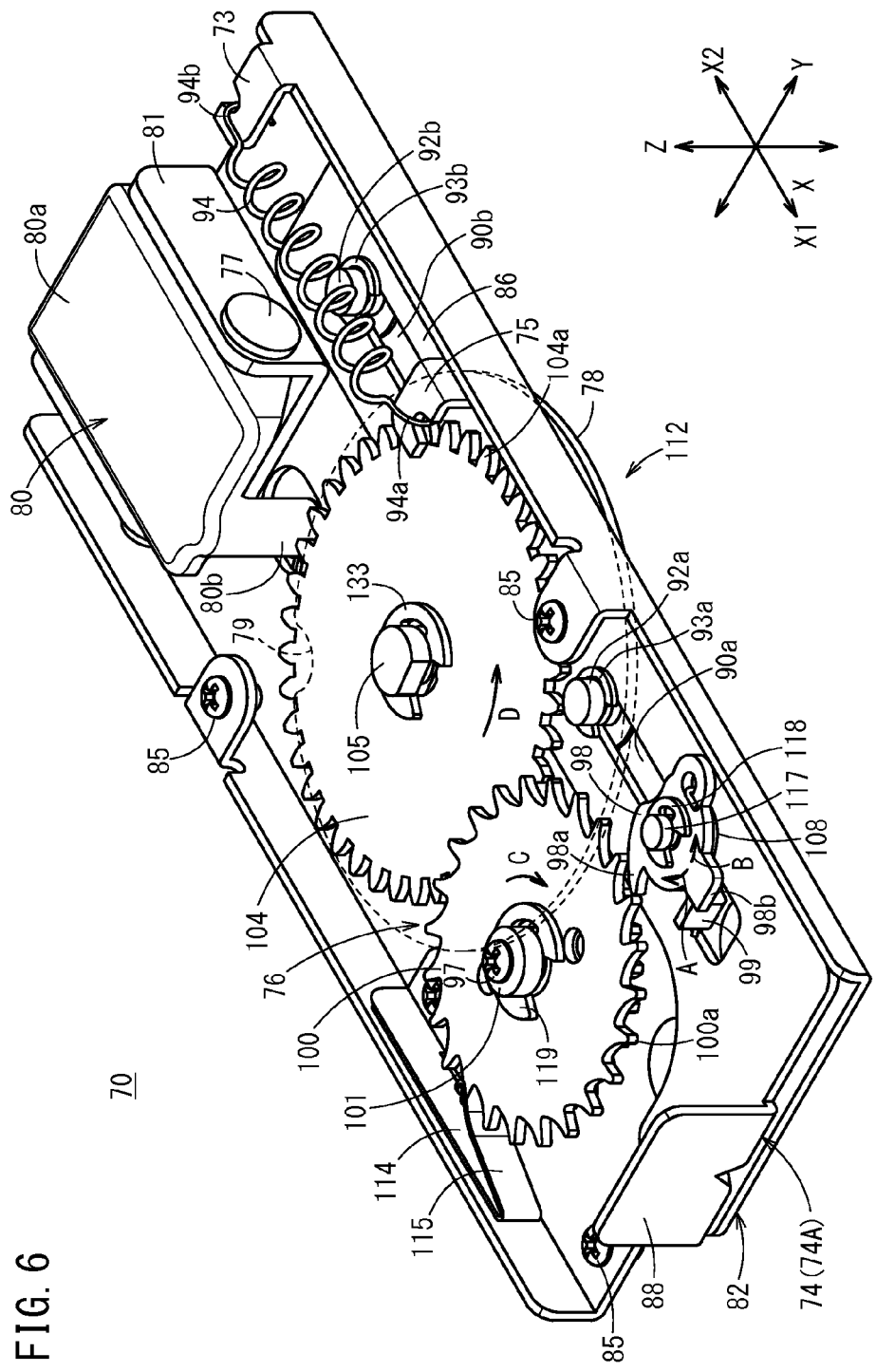
FIG. 6 is a view showing a condition in which the slider is advanced in the number of times limiting mechanism.

When the drive unit 22 is attached with respect to the handle 14 of the manipulator main body 11A in such an unused state, the pressed member 88 of the operating body 74 is pressed forwardly (in the X1 direction) by a portion (e.g., the distal end part of the housing 48) of the drive unit 22. As a result, as shown in FIG. 6, the operating body 74 moves to an advanced position. Accompanying the advancement of the operating body 74, the pawl member 98 disposed on the operating body 74 also is advanced forward. The engagement pawl 98a of the advancing pawl member 98 presses the teeth 100a of the ratchet wheel 100. Consequently, the ratchet wheel 100 is rotated by one tooth portion in the C direction. Upon rotation of the ratchet wheel 100, accompanying elastic deformation of the latch piece 115, the teeth 100a of the ratchet wheel 100 overcome the latch piece 115 by one tooth portion.

Together with rotation of the ratchet wheel 100, the first gear 102 also rotates in the C direction. Accompanying rotation of the first gear 102, the second gear 104 that is enmeshed with the first gear 102 rotates in the D direction, together with the rotating body 78 that is connected coaxially with the second gear 104 also rotating in the D direction. Consequently, the notch 79 provided on the rotating body 78 is displaced by a predetermined amount in the D direction. In the state shown in FIG. 6, the abutment 80b of the stopper 80 stays in abutment against the outer circumferential portion of the rotating body 78, and therefore, the stopper 80 remains in the non-regulating condition.

When the drive unit 22 is removed from the handle 14, the operating body 74 returns to the retracted position. More specifically, accompanying movement of the drive unit 22 rearwardly (in the X2 direction), pressing by the drive unit 22 with respect to the pressed member 88 is released, and under the elastic force of the return spring 94, the operating body 74 is moved in a rearward direction. Together with such rearward movement of the operating body 74, although the teeth 100a of the ratchet wheel 100 are pushed back by the pawl member 98 disposed on the operating body 74, by an engaging action of the latch piece 115, the ratchet wheel 100 is prevented from rotating in a direction opposite to the C direction. Therefore, at the time of retracted movement of the operating body 74, the notch 79 provided on the rotating body 78 does not return to its former position.

Further, at the time of retracted movement of the operating body 74, due to turning of the pawl member 98 in the B direction in opposition to the elastic force of the pawl biasing member 108 in the A direction, the teeth 100a of the ratchet wheel 100 are overcome by one tooth portion. When the engagement pawl 98a of the pawl member 98 overcomes the teeth 100a of the ratchet wheel 100 by one tooth portion, the pawl member 98 is rotated in the A direction by the elastic force of the pawl biasing member 108, and stops at the position of abutment between the abutting projection 98b and the latching piece 99.

In the number of times limiting mechanism 70, until the predetermined number of times (number of times usage limit of the manipulator main body 11A) is reached, the operations described above are repeated with each attachment and detachment of the drive unit 22 with respect to the handle 14. Consequently, with each attachment and detachment of the drive unit 22, the notch 79 provided on the rotating body 78 moves by a predetermined amount in the D direction.

Figure 7:
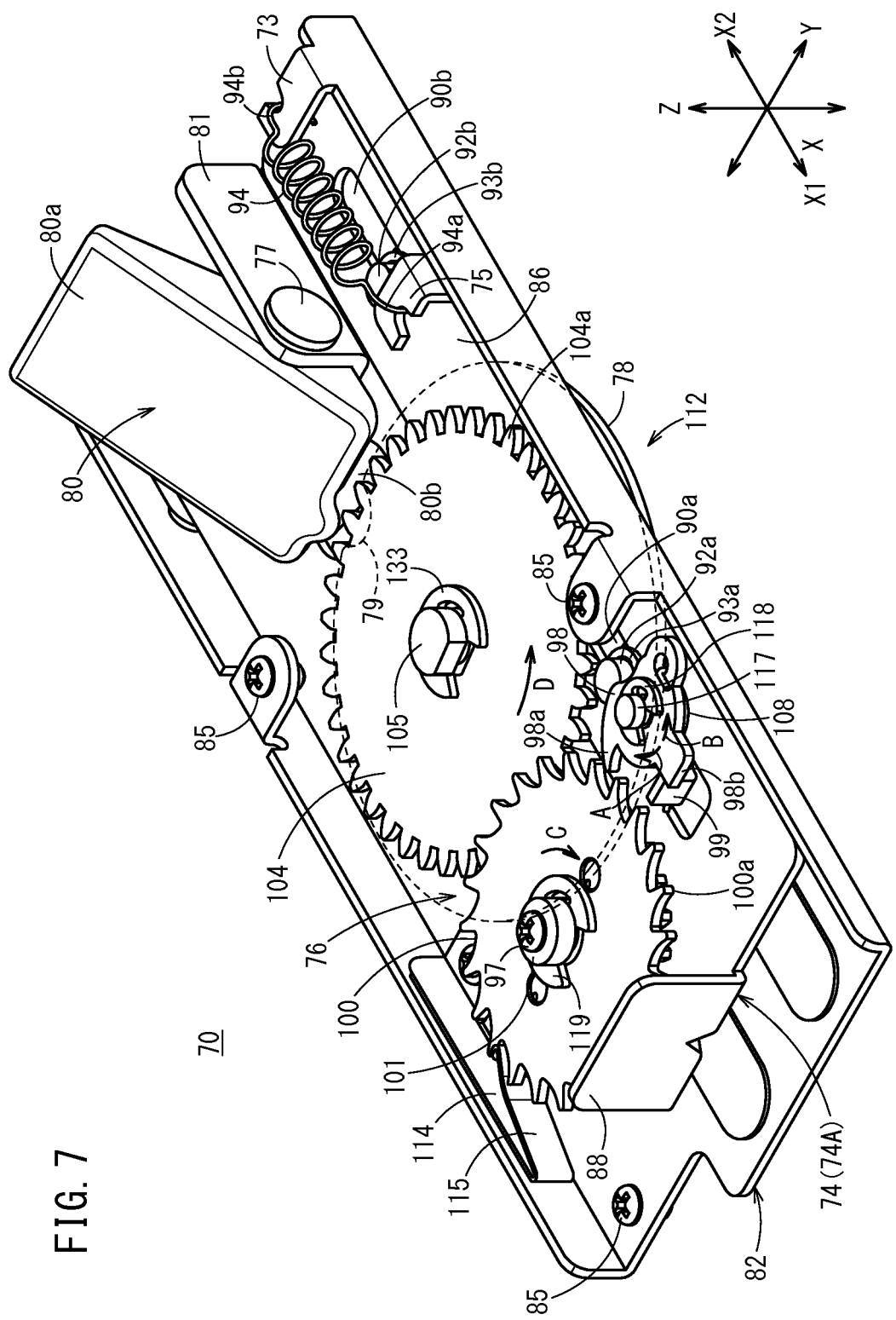
FIG. 7 is a perspective view showing a state in which the attachment and detachment prevention function is triggered in the number of times limiting mechanism.
Figure 8:
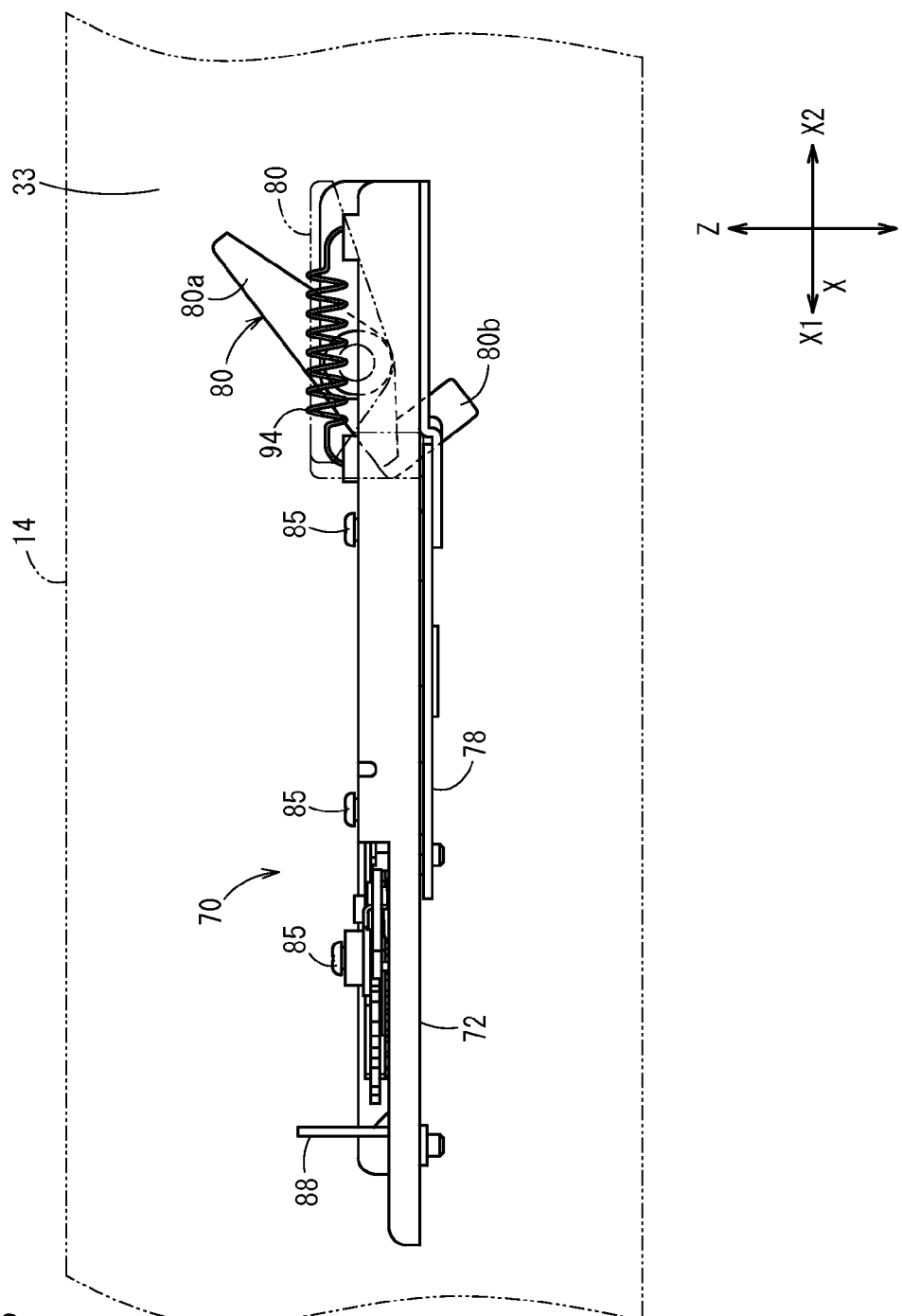
FIG. 8 is a side view showing a state in which the attachment and detachment prevention function is triggered in the number of times limiting mechanism.

In addition, when attachment and detachment of the drive unit 22 with respect to the handle 14 is repeated, and the number of times of attachment and detachment reaches the predetermined number of times, whereupon the notch 79 comes to the position of the abutment 80b of the stopper 80, regulation of displacement with respect to the stopper 80 by the rotating body 78 is released. As a result, along with the abutment 80b entering into the notch 79, as shown in FIGS. 7 and 8, the stopper 80 rises at an angle, and arrives at the regulating condition. In FIG. 8, the stopper 80 in the non-regulating condition thereof is shown by phantom lines (two dot dashed lines).

In the regulating condition, the stopper 80 projects into the movement path (in the present illustrated example, inside the installation hole 33) of the drive unit 22 when the drive unit 22 is attached to the handle 14. Consequently, even if it is attempted to attach the drive unit 22 to the handle 14, the drive unit 22 comes into abutment with the stopper 80, at an intermediate location during movement of the drive unit 22 in a distal end direction with respect to the handle 14. Therefore, it is impossible for the drive unit 22 to be moved further forwardly beyond this point. As a result, attachment of the drive unit 22 with respect to the handle 14 is prevented.

As described above, with the manipulator 10A according to the present embodiment, if the number of times that the drive unit 22 has been attached and detached with respect to the handle 14 reaches a predetermined number of times (number of times usage limit of the manipulator main body 11A), it becomes impossible for the drive unit 22 to be attached to the handle 14. Stated otherwise, use of the manipulator main body 11A in excess of the number of times usage limit can be forcibly restricted.

In the case of the present embodiment, the number of times limiting mechanism 70 includes the operating body 74 and the counter mechanism 112, and when the counter mechanism 112 has been operated the predetermined number of times from an initial state thereof, attachment of the drive unit 22 with respect to the handle 14 is prevented. In accordance with the above configuration, by providing the counter mechanism 112 and the operating body 74, which is interlinked mechanically with attachment and detachment of the drive unit 22, the number of times of attachment and detachment is reliably counted. Therefore, when the predetermined number of times is reached, it is possible for the attachment prevention function to be triggered reliably.

In the present embodiment, in the regulating condition, the stopper 80 projects into the movement path of the drive unit 22 when the drive unit 22 is attached to the handle 14. According to this structure, even if it is attempted to attach the drive unit 22 to the handle 14 when the stopper 80 is in the regulating condition, since the drive unit 22 becomes caught on or engaged with the stopper 80, attachment of the drive unit 22 can physically be prevented. Accordingly, use of the manipulator main body 11A in excess of the number of times usage limit can reliably be prevented.

In the present embodiment, the operating body 74 is constituted as the slider 74A that can be advanced and retracted accompanying attachment and detachment of the drive unit 22 with respect to the handle 14. According to this configuration, attachment and detachment of the drive unit 22 can be reliably detected mechanically, and the counter mechanism 112 can be operated.

In the present embodiment, since the return spring 94 (operating body biasing means) is included, which biases the operating body 74 toward the retracted position, when the drive unit 22 is removed from the handle 14, the operating body 74 can be restored reliably to the retracted position (first position). Consequently, with each attachment and detachment of the drive unit 22, the counter mechanism 112 can reliably be operated by a predetermined amount.

In the present embodiment, the operating body 74 is linked mechanically by attachment and detachment of the drive unit 22, and movements of the operating body 74 are transmitted to the rotating body 78 through the intermediate transmission mechanism 76. When the number of attachments and detachments reaches the predetermined number of times, the regulating condition is brought about in which the stopper 80 projects into the movement path of the drive unit 22. In this condition, even if it is attempted to attach the drive unit 22 to the handle 14, since the drive unit 22 becomes caught on or engaged with the stopper 80, attachment of the drive unit 22 can physically be prevented. Accordingly, use of the manipulator main body 11A in excess of the number of times usage limit can reliably be prevented.

In the present embodiment, each of the operating body 74, the intermediate transmission mechanism 76, and the rotating body 78 are formed by plate-shaped members, and the stopper 80 is changed from the non-regulating condition to the regulating condition accompanying a tilting movement of the stopper 80 from an initial posture. According to this configuration, the number of times limiting mechanism 70 can be given a thin profile, and the installation volume within the handle 14 can be reduced. Consequently, an increase in scale of the handle 14 together with arrangement of the number of times limiting mechanism 70 therein can be suppressed.

In the present embodiment, the intermediate transmission mechanism 76 includes a plurality of mutually intermeshed gears (the first gear 102 and the second gear 104). According to this configuration, the amount of rotation of the rotating body 78, corresponding to the displacement amount of the operating body 74 at the time of attachment and detachment of the drive unit 22 with respect to the handle 14, can be adjusted by the gear ratio of the gears. Therefore, by adjusting the gear ratio, the number of times (predetermined number of times) to trigger the attachment prevention function can easily be set.

In the present embodiment, in a state in which the number of times of attachment and detachment is less than the predetermined number of times, the abutment 80b provided on the stopper 80 abuts against the rotating body 78, whereby the stopper 80 is retained in the non-regulating condition in opposition to a biasing force of the stopper biasing member 110. On the other hand, in a state in which the number of times of attachment and detachment has reached the predetermined number of times, the abutment 80b provided on the stopper 80 is capable of entering into the notch 79. According to this configuration, a mechanism can easily be constructed in which the stopper 80 is not operated in a state in which the number of times of attachment and detachment is less than the predetermined number of times, and the stopper 80 is operated when the predetermined number of times is reached.

In the above-described manipulator main body 11A, instead of the number of times limiting mechanism 70, the number of times limiting mechanism 120 according to the modification shown in FIGS. 9 through 12C may be adopted. The number of times limiting mechanism 120 provided on the handle 14 serves to prevent attachment of the drive unit 22 with respect to the handle 14, in the event that the number of times of attachment and detachment of the drive unit 22 with respect to the handle 14 has reached a predetermined number of times.

More specifically, the number of times limiting mechanism 120 includes an operating body 122 capable of sliding in forward and rearward directions with respect to the handle 14, a first pawl member 124 disposed swingably with respect to the operating body 122, a first biasing member 126 that elastically biases the operating body 122 and the first pawl member 124, a linear rack member 128 that engages with the first pawl member 124, a second pawl member 130 that engages with the rack member 128 on a surface that differs from the surface with which the first pawl member 124 engages, and a second biasing member 132 that elastically biases the second pawl member 130.

Figure 9:
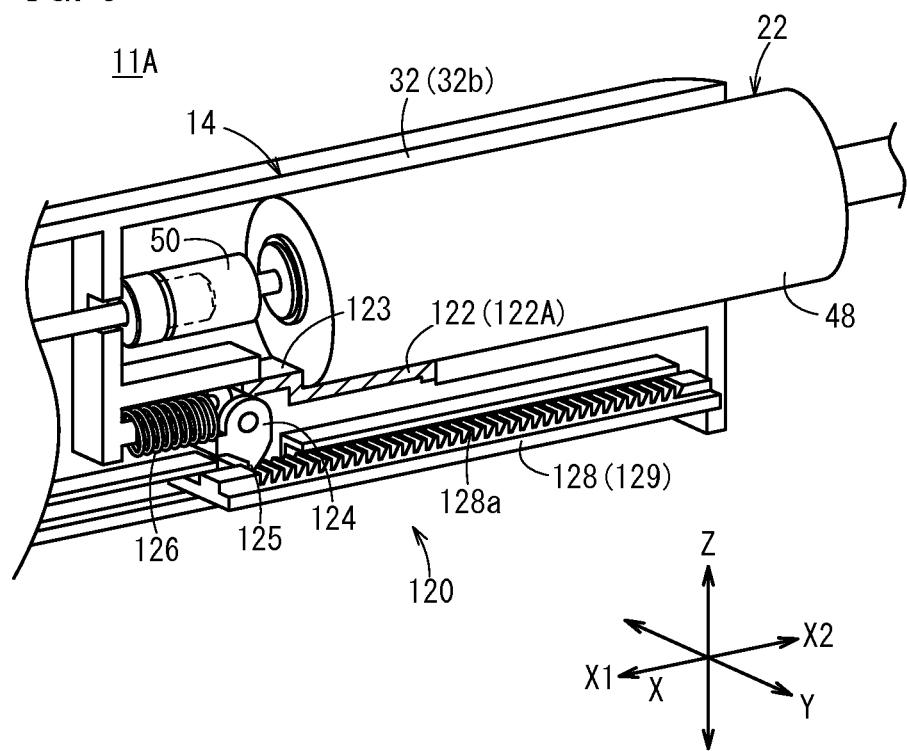
FIG. 9 is a schematic perspective view of a number of times limiting mechanism according to a modification.
Figure 10:
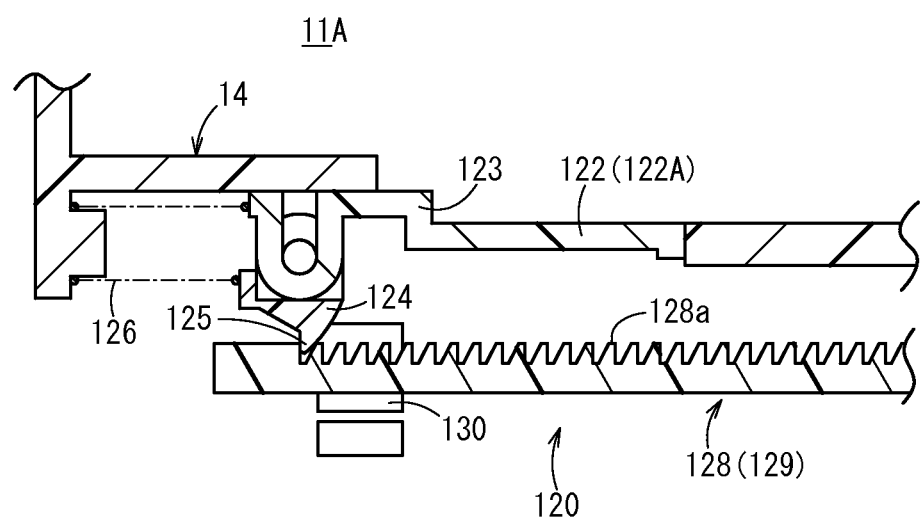
FIG. 10 is a cross-sectional view of the number of times limiting mechanism according to the modification.

The operating body 122 is linked mechanically with attachment and detachment of the drive unit 22 with respect to the handle 14. More specifically, accompanying attachment of the drive unit 22 with respect to the handle 14, the operating body 122 of the present illustrated example is pressed by the drive unit 22, and is displaced from a retracted position (first position) to an advanced position (second position). Further, accompanying removal of the drive unit 22 from the handle 14, the operating body 122 returns from the advanced position to the retracted position. FIGS. 9 and 10 show the operating body 122 in the retracted position.

In this manner, the operating body 122 in the present illustrated example is constituted as a slider 122A that can be advanced and retracted accompanying attachment and detachment of the drive unit 22 with respect to the handle 14. A step-shaped pressed member 123 is disposed on the operating body 122 of the present illustrated example. The operating body 122 is biased elastically at all times toward the retracted position (X2 direction) by the first biasing member 126.

The first pawl member 124 is capable of swinging through a shaft with respect to the operating body 122, and a portion thereof disposed more downwardly than the pivotal center is biased elastically at all times in a rearward direction by the first biasing member 126. The first engagement pawl 125 is disposed on the first pawl member 124.

The rack member 128 is disposed slidably in forward and rearward directions (the X direction) of the handle 14. First teeth 128a (see FIGS. 9 and 10) and second teeth 128b (see FIG. 11B) are disposed on the rack member 128. In the present illustrated example, the first teeth 128a are disposed on an upper surface of the rack member 128, and the second teeth 128b are disposed on a side surface of the rack member 128. The first engagement pawl 125 of the first pawl member 124 engages with the first teeth 128a of the rack member 128. In the number of times limiting mechanism 120, the rack member 128 constitutes a counter mechanism 129 that is operated by a predetermined amount with each operation of the operating body 122.

The second pawl member 130 is swingably disposed through a shaft on the handle 14. A second engagement pawl 131 is disposed on the second pawl member 130. The second engagement pawl 131 engages with the second teeth 128b of the rack member 128. The second biasing member 132 elastically biases the second pawl member 130 toward the side of the rack member 128.

In a state in which the drive unit 22 has not been attached and detached even one time with respect to the manipulator main body 11A, or in other words, in an unused state of the manipulator main body 11A, the number of times limiting mechanism 120 is in an initial state, as shown in FIG. 10. When the drive unit 22 is attached with respect to the handle 14 of the manipulator main body 11A in such an unused state, the pressed member 123 of the operating body 122 is pressed forwardly by a portion (e.g., the distal end part of the housing 48) of the drive unit 22.

Figure 11A:
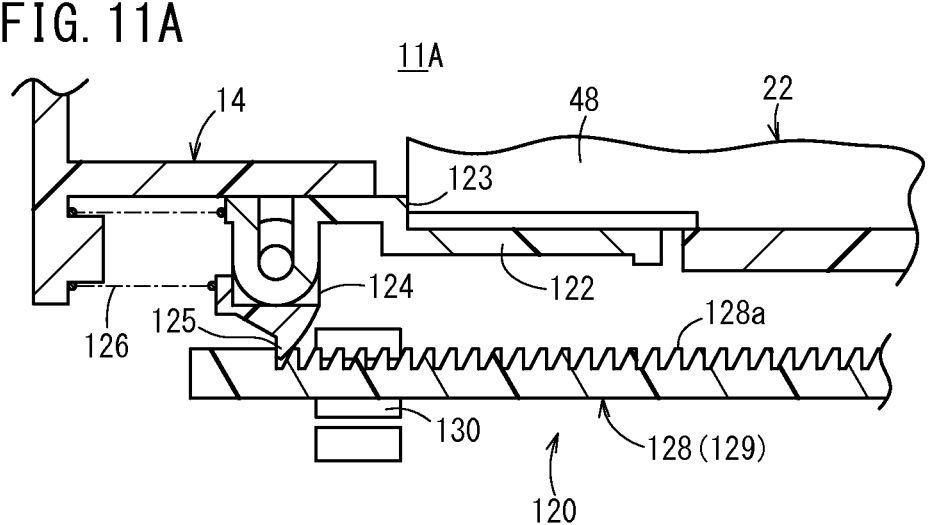
FIG. 11A is a schematic cross-sectional view of the number of times limiting mechanism according to the modification at a time when the drive unit is attached.
Figure 11B:
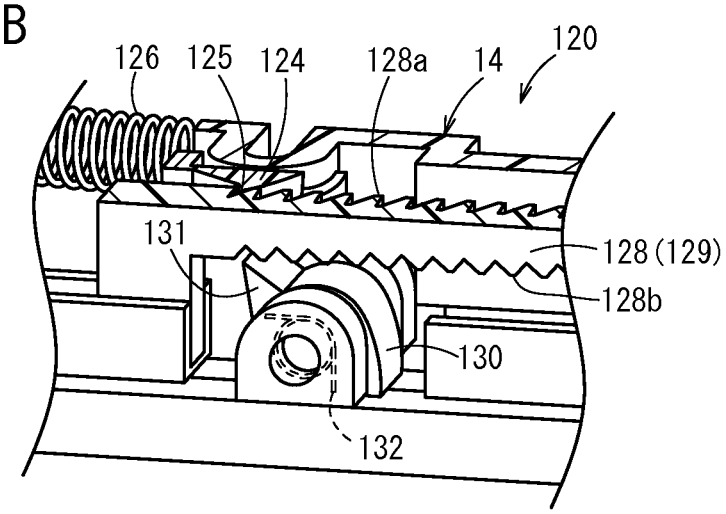
FIG. 11B is a first explanatory drawing for describing an operation of a second pawl member when a rack member in the number of times limiting mechanism according to the modification is advanced.
Figure 11C:
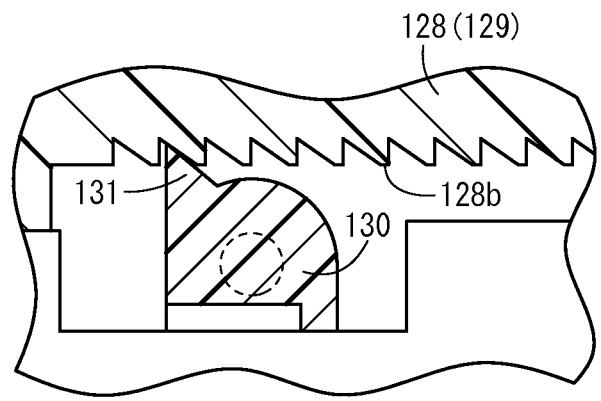
FIG. 11C is a second explanatory drawing for describing an operation of the second pawl member when the rack member in the number of times limiting mechanism according to the modification is advanced.

As a result, as shown in FIG. 11A, the operating body 122 moves to an advanced position. Accompanying the advancement of the operating body 122, the first pawl member 124 disposed on the operating body 122 also is advanced forward. The first engagement pawl 125 of the advancing first pawl member 124 presses the first teeth 128a of the rack member 128 in a forward direction (X1 direction). Accordingly, the rack member 128 is advanced forward by one tooth portion. In the process of advancement, as shown in FIG. 11B, the second pawl member 130 that engages with the second teeth 128b is tilted in opposition to the elastic force of the second biasing member 132. In addition, as shown in FIG. 11C, when the rack member 128 advances by one tooth portion, due to the elastic force of the second biasing member 132, the second pawl member 130 is restored to its initial posture, whereupon the second engagement pawl 131 enmeshes with the next one of the second teeth 128b (the adjacent second tooth 128b on the rearward side).

When the drive unit 22 is removed from the handle 14, the operating body 122 returns to the retracted position. More specifically, accompanying movement of the drive unit 22 rearwardly, pressing by the drive unit 22 with respect to the pressed member 123 is released, and under the elastic force of the first biasing member 126, the operating body 122 is moved in a rearward direction.

Figure 12A:
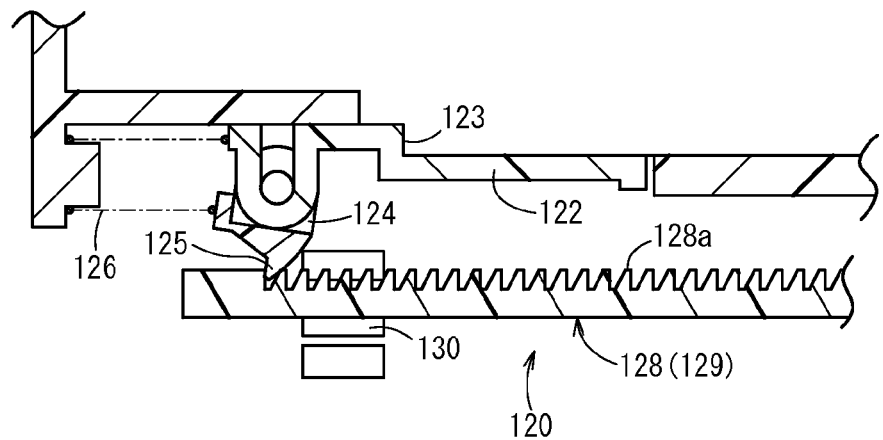
FIG. 12A is a schematic cross-sectional view for describing an operation of the number of times limiting mechanism according to the modification at a time when the drive unit is detached.
Figure 12B:
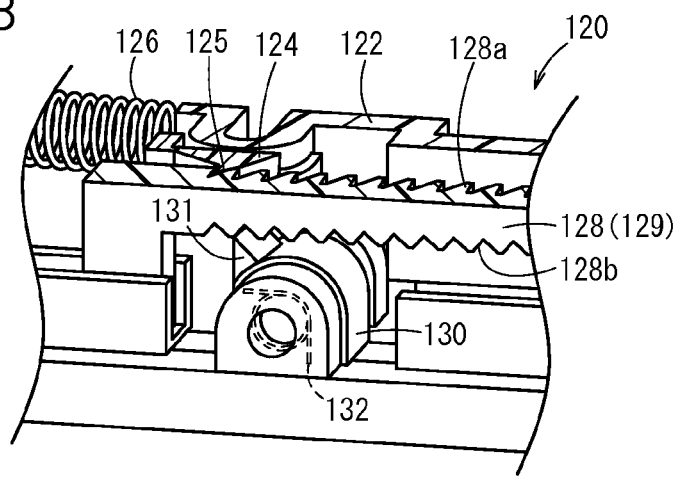
FIG. 12B is a drawing for describing an operation of the second pawl member of the number of times limiting mechanism according to the modification at a time when the drive unit is detached.

During the process of rearward movement of the operating body 122, as shown in FIG. 12A, although the first pawl member 124 is moved rearwardly, since the first engagement pawl 125 is pressed by the first teeth 128a of the rack member 128, the first pawl member 124 undergoes rotation. At this time, as shown in FIG. 12B, since the second engagement pawl 131 of the second pawl member 130 and the second teeth 128b of the rack member 128 are enmeshed, the rack member 128 does not revert to movement in a rearward direction.

Figure 12C:
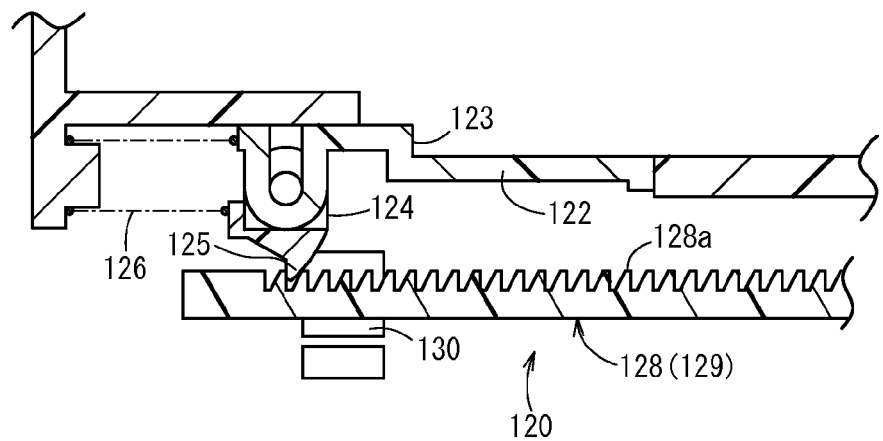
FIG. 12C is a drawing for describing an operation of a first pawl member of the number of times limiting mechanism according to the modification at a time when the drive unit is detached.

In addition, as shown in FIG. 12C, when the operating body 122 returns to its former position (retracted position), since the first pawl member 124 is pressed to the lower side beyond the center of rotation by the first biasing member 126, the first engagement pawl 125 enmeshes with the next one of the first teeth 128a.

In the number of times limiting mechanism 120, until the predetermined number of times (number of times usage limit of the manipulator main body 11A) is reached, the operations described above are repeated with each attachment and detachment of the drive unit 22 with respect to the handle 14. Consequently, with each attachment and detachment of the drive unit 22, the rack member 128 moves forward. In addition, when attachment and detachment of the drive unit 22 with respect to the handle 14 is repeated, at a point in time at which the number of times of attachment and detachment has reached the predetermined number of times, a portion (e.g., a distal end part) of the rack member 128 abuts against a wall in the interior of the handle 14, and further advancement of the rack member 128 beyond this point becomes impossible.

In such a condition, in which advancement of the rack member 128 is prevented, advancement of the operating body 122 also is prevented. Consequently, even if it is attempted to attach the drive unit 22 to the handle 14, at a point in time at which the drive unit 22 is in abutment against the pressed member 123 of the operating body 122, at an intermediate location during movement of the drive unit 22 in a distal end direction with respect to the handle 14, it is impossible for the drive unit 22 to be moved any further in the distal end direction. As a result, attachment of the drive unit 22 with respect to the handle 14 is prevented.

Figure 13:
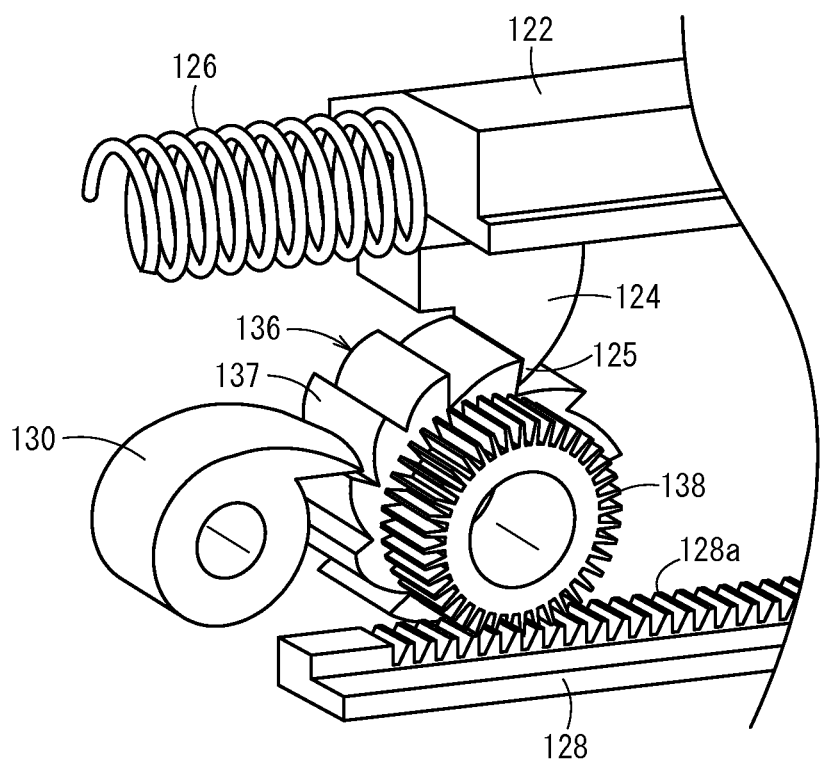
FIG. 13 is a schematic perspective view showing a structural example in which a gear member is provided in the number of times limiting mechanism according to a modification.

In the aforementioned number of times limiting mechanism 120, in the case it is difficult to ensure that the strokes of the rack member 128 will reach the set number of times from the initial position, the structure shown in FIG. 13 may be adopted. In FIG. 13, a gear member 136 (speed reducing mechanism) having a plurality of gears (a first gear 137 and a second gear 138) is arranged between the first pawl member 124 and the rack member 128. The second gear 138 is of a smaller diameter than the first gear 137. The first engagement pawl 125 of the first pawl member 124 enmeshes with the first gear 137 of the gear member 136. The second gear 138 of the gear member 136 enmeshes with the first teeth 128a of the rack member 128.

In the case of this configuration, along with advancement of the first pawl member 124, the gear member 136 is rotated. The rotation of the gear member 136 is converted into linear motion in the rearward direction (X2 direction) of the rack member 128 via the second gear 138 and the first teeth 128*a*. At this time, from the fact that a decelerating action is carried out due to the second gear 138 being smaller in diameter than the first gear 137, the amount of linear displacement (absolute value) of the rack member 128 is smaller than the linear displacement amount (absolute value) of the first pawl member 124. Consequently, it can easily be ensured that the strokes of the rack member 128 will reach the set number of times from the initial position.

In this case, as shown in FIG. 11B, the second engagement pawl 131 of the second pawl member 130 may enmesh with the second teeth 128*b* of the rack member 128. Alternatively, as shown in FIG. 13, a function may be possessed in which, by enmeshment between the first gear 137 of the gear member 136 and the second engagement pawl 131 of the second pawl member 130, a reversal in movement of the rack member 128 is prevented.

In the number of times limiting mechanism 120, at a state in which the number of times of attachment and detachment has reached the predetermined number of times, if it is attempted to forcibly attach the drive unit 22 to the handle 14, there is a concern that an excessive load will be applied to the rack member 128. In such a case, the configuration shown in FIGS. 14A and 14B may be adopted.

As shown in FIG. 14A, in a state prior to the number of times of attachment and detachment reaching the predetermined number of times, the lock member 142 is pressed into abutment against the rack member 128 by a biasing member 140 (a spring or the like). Together with the attachment and detachment of the drive unit 22 being repeated, the rack member 128 advances forward, and upon the rack member 128 being advanced up to the position at which the number of times of attachment and detachment reaches the predetermined number of times, the lock member 142 is released from the rack member 128. As a result, as shown in FIG. 14B, the lock member 142 is displaced toward the operating body 122 by the elastic force of the biasing member 140, and engages with the operating body 122. In such a condition, in which the lock member 142 has engaged with the operating body 122, movement of the operating body 122 in the X direction is prevented.

In a state in which the number of times of attachment and detachment has reached the predetermined number of times, even if it is attempted to forcibly attach the drive unit 22 to the handle 14, due to engagement of the lock member 142 with the operating body 122, further advancement of the operating body 122 is impossible. Consequently, imposition of excessive loads on the lock member 142 is suitably prevented.

Instead of the lock member 142, for example, as shown by the phantom lines in FIGS. 14A and 14B, a stopper 143 may be provided, which is operated to project into the insertion opening of the drive unit 22 in the handle 14, when the number of times of attachment and detachment has reach the predetermined number of times.

Figure 15:
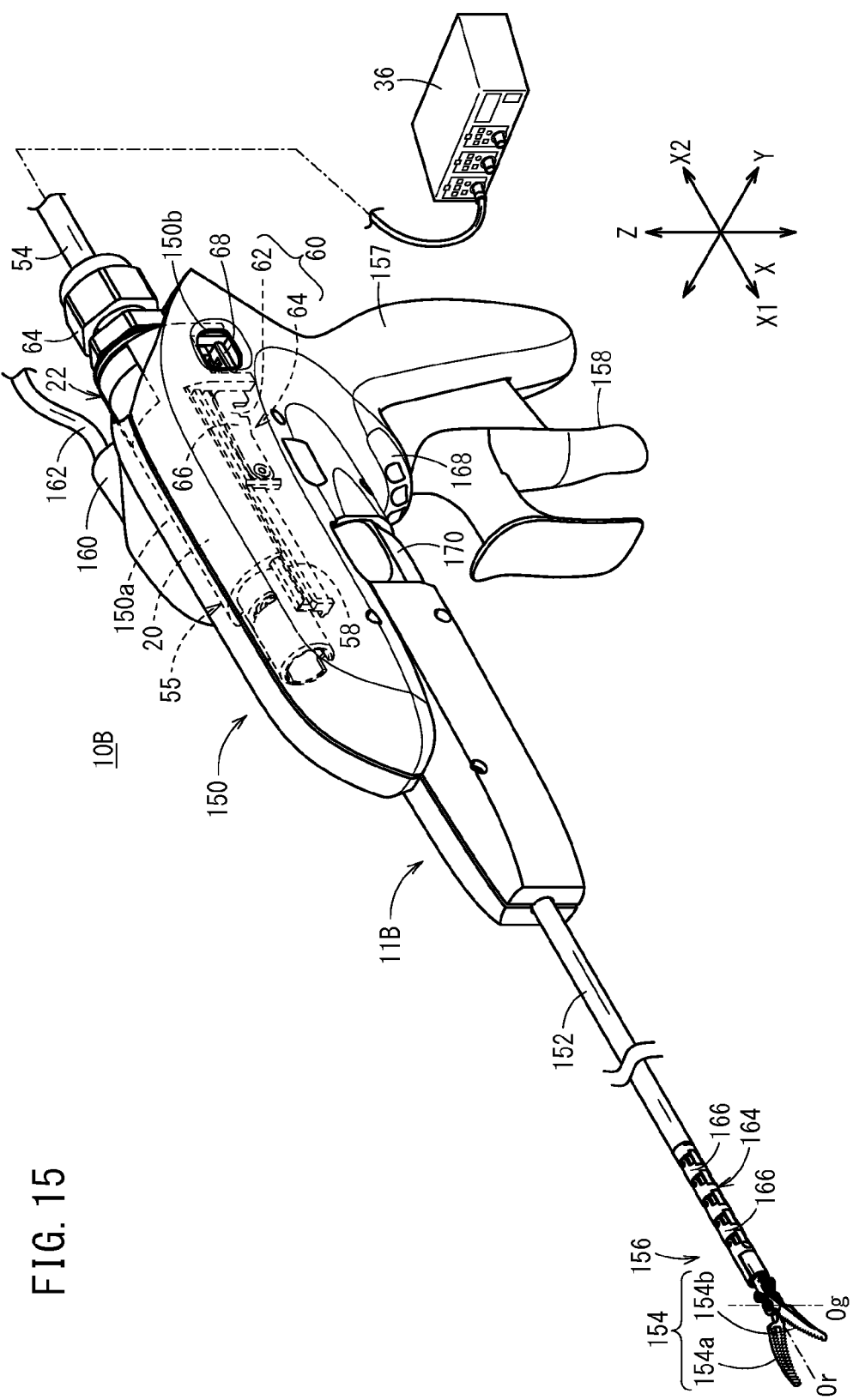
FIG. 15 is a perspective view with partial omission of a medical manipulator according to another embodiment of the present invention.
Figure 16:
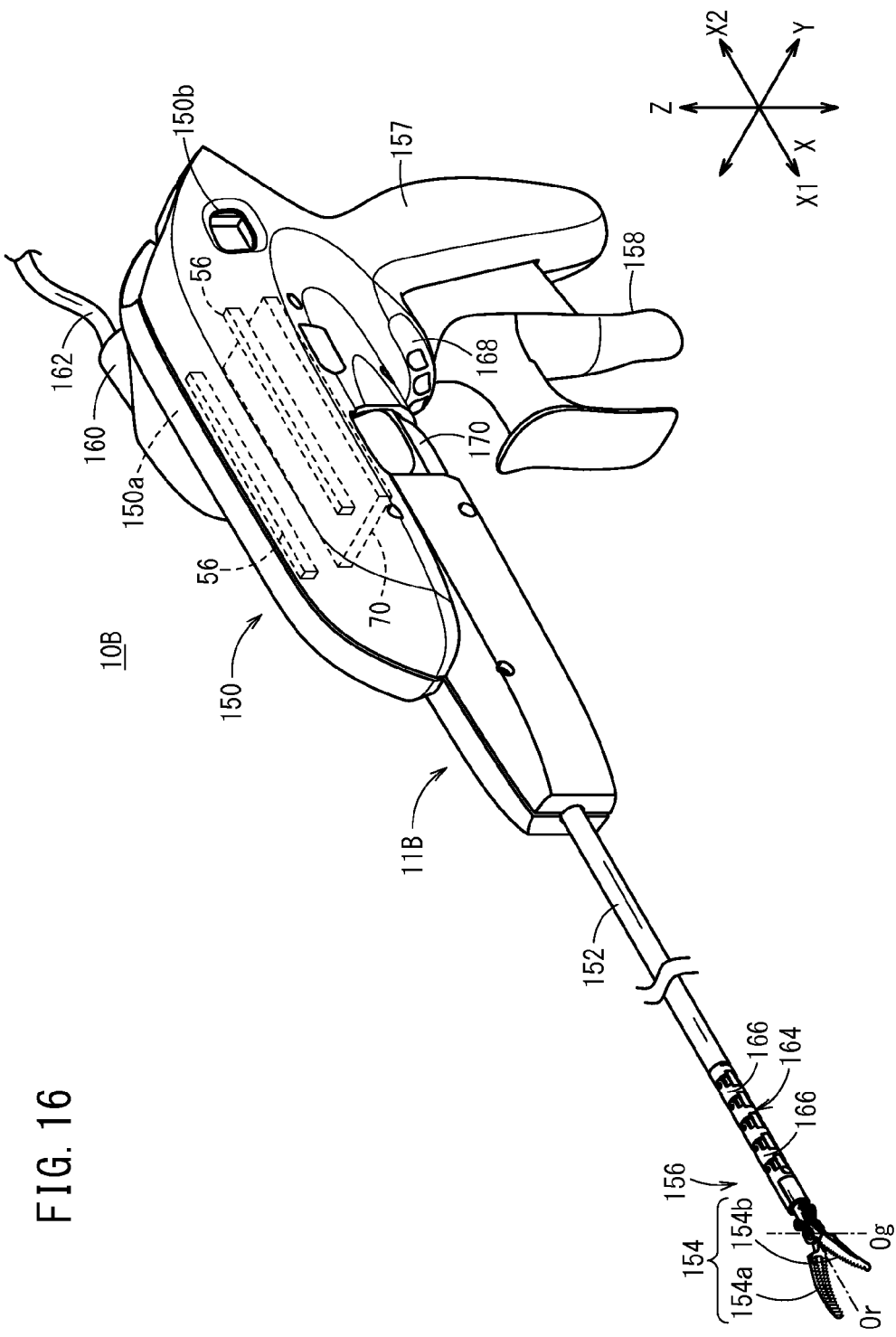
FIG. 16 is a perspective view with partial omission of a manipulator main body in the medical manipulator shown in FIG. 15.

The drive unit 22, which is constructed as described above, can be mounted and used not only with the manipulator main body 11A, which is constituted as a needle driver, but also with a manipulator main body 11B, which is constituted as an electrosurgical scalpel, as shown in FIGS. 15 and 16. In this case, by combining together the manipulator main body 11B and the drive unit 22, an electrosurgical scalpel type medical manipulator 10B (hereinafter referred to in an abbreviated form as a "manipulator 10B"), which is driven by the motor 20, is constructed.

The manipulator main body 11B comprises a handle 150 on which a plurality of input operating members are provided, a shaft 152 that extends from the handle 150, and a distal end working unit 156 disposed on a distal end of the shaft 152 and including a gripper 154 (end effector).

The manipulator main body 11A shown in FIG. 1 is of an overall stick-like (rod-like) shape suitable for use as a needle driver. In contrast thereto, with the manipulator main body 11B shown in FIG. 15, a grip 157 that projects downwardly on a lower part of the handle 150 is provided, and the handle 150 is in the shape of a pistol as a whole, having a shape that is suitable for use as an electrosurgical scalpel. Further, such a pistol type handle shape also is suitable for use with scissors, a grasping implement, and a peeling implement, etc.

The gripper 154 is capable of making opening and closing movements, and serves as a portion for gripping biological tissue, and cauterizing the biological tissue by conduction of current through the tissue. The gripper 154 of the present illustrated example includes a first gripper member 154*a* and a second gripper member 154*b*, which are capable of swinging or pivoting in mutually opposite directions about an opening and closing operation axis Og.

The manipulator main body 11B may be constructed as a bipolar type of electrical scalpel in which the first gripper member 154*a* and the second gripper member 154*b* are electrically energized at different polarities, or a monopolar type of electrical scalpel in which either one of the first gripper member 154*a* or the second gripper member 154*b*, or both is electrically energized.

The opening and closing operation of the gripper 154 is carried out by mechanically transmitting the operation of a lever 158, which is provided on the handle 150, to the distal end working unit 156 through a non-illustrated opening/closing drive transmission system. More specifically, in the present illustrated example, the lever 158 is constructed as a manual operating member, and opening and closing operations of the gripper 154 are performed not by a motor drive, but by a manual drive on the basis of an operating force from the operator.

The lever 158 is disposed for displacement in forward and rearward directions with respect to the grip 157, such that when the lever 158 is pressed out forwardly relative to the grip 157, the gripper 154 opens, and when the lever 158 is drawn in rearwardly relative to the grip 157, the gripper 154 is closed. A structure may also be adopted in which the opening/closing operation of the gripper 154 is performed by a motor drive.

In the manipulator 10B, in accordance with the combination of the manipulator main body 11B and the drive unit 22, a power supplying connector 160 is connected to the handle 150, whereby the manipulator 10B can be used as an electrosurgical scalpel. The power supplying connector 160 is connected to a non-illustrated high frequency power supply device through an energizing cable 162, and by the high frequency power supply device, a high frequency voltage is applied in order to electrically energize the gripper 154.

The distal end working unit 156 is capable of being tilted laterally (yaw operation) by a bending portion 164 disposed on a distal end of the shaft 152. The bending portion 164 has a plurality of joint members 166, which are coupled rotatably within a predetermined angular range to one another. Although in a state in which the joint members 166 are aligned coaxially, the bending portion 164 exhibits a linear shape, when the adjacent joint members 166 themselves are mutually tilted, the bending portion 164 exhibits a curved shape as a whole.

The tilting operation of the distal end working unit 156 is carried out by the controller 36 controlling driving of the motor 20 based on an operation made with respect to a tilting switch 168 provided on the handle 150, and by mechanically transmitting the driving force of the motor 20 to the distal end working unit 156 through the handle 150 and the shaft 152. More specifically, in the present illustrated example, the tilting switch 168 is constructed as an electrical operating member, and the tilting operation of the distal end working unit 156 is performed by a motor drive.

The distal end working unit 156, at a portion thereof located more toward the distal end side than the bending portion 164, is capable of executing a rolling operation about the roll axis Or. The rolling operation is carried out by mechanically transmitting a rotating operation made with respect to a rotating knob 170 (input operating member), which is provided on the handle 150, to the distal end working unit 156 through a non-illustrated rolling drive transmission system. More specifically, in the present illustrated example, the rotating knob 170 is constructed as a manual operating member, and the rolling operation of the distal end working unit 156 is performed not by a motor drive, but by a manual drive on the basis of an operating force from the operator. A structure may also be adopted in which the rolling operation of the distal end working unit 156 is performed by a motor drive.

On an upper end side of the handle 150, a mounting hole 150a is provided, which opens rearwardly. The drive unit 22 is inserted into the mounting hole 150a, and thus can be mounted with respect to the handle 150. More specifically, the drive unit 22 is capable of being attached to and detached from the proximal end side of the handle 150. In a state in which the drive unit 22 is mounted in the handle 150, so that operating tabs 68, which are disposed on the drive unit 22, can be touched and operated by the user, the operating tabs 68 protrude through openings 150b provided on side surfaces on left and right sides of the handle 150.

As shown in FIG. 16, guide rails 56, which are similar to those of the handle 14 in the manipulator main body 11A, are provided in the handle 150. Consequently, under a guiding action of a guide mechanism 55 (see FIG. 15) made up from the guide rails 56 and the guide receiving members 58, the drive unit 22 can move smoothly relative to the handle 150, and the drive unit 22 can be mounted easily and reliably at an accurate positional relationship with respect to the handle 150.

Although omitted from illustration in FIGS. 15 and 16, a driven coupling, which is similar to the driven coupling provided on the handle 14 of the manipulator main body 11A, is provided on the handle 150. Consequently, in a state in which the drive unit 22 is mounted with respect to the handle 150, by engagement of the drive coupling 50 and the driven coupling, a driving force of the motor 20 can be transmitted reliably to the handle 150.

Although illustration thereof is omitted in FIGS. 15 and 16, handle-side terminals are provided on the handle 150. In a state in which the drive unit 22 is attached to the handle 150, the handle-side terminals and the unit-side terminals provided on the drive unit 22 are placed in contact. According to this structure, the operating state of the tilting switch 168 can be detected by the controller 36, and the controller 36 can appropriately control driving of the motor 20.

On the handle 150, similar to the handle 14 shown in FIG. 1 and the like, an engagement member 62 is provided that is capable of engaging with the lever member 66 disposed on the drive unit 22. Accordingly, together with attachment of the drive unit 22 with respect to the handle 150, a condition (locked state) is brought about in which movement of the drive unit 22 in the proximal end direction relative to the handle 150 is prevented.

In this manner, the drive unit 22 can be attached and detached with respect to manipulator main bodies 11B (forceps portions) having different functions and shapes, and in the attached state, transmission of a driving force of the motor 20 to the handles 14, 150, electrical connections between the handles 14, 150 and the drive unit 22, and preventing the drive unit 22 from moving with respect to the handles 14, 150 can reliably be achieved.

The form of the manipulator main bodies 11A, 11B, which enable attachment and detachment of the drive unit 22, is not limited to the two forms (needle driver, electrosurgical scalpel) described above, and forms having other different functions and shapes, for example, scissors, a grasping forceps, or the like, may be provided. In addition, a suction device, a cleaning device, an energy device, etc., may be provided.

As described above, with the manipulators 10A, 10B, the drive unit 22 can be mounted easily and reliably with respect to handles 14, 150 having different shapes and functions, and together therewith, based on an operation of an input operating member (rolling switch 28, tilting switch 168) disposed on the handles 14, 150, the motor 20 can be driven, and the distal end working unit 18 can be operated by the driving force thereof.

In the foregoing manner, with the manipulators 10A, 10B, because the drive unit 22 including the motor 20 is capable of attachment and detachment with respect to the handle 14, there is no need for a drive source to be provided for each of handles 14 having different shapes and functions. More specifically, in the manipulators 10A, 10B of the present invention, a common drive unit 22 can be mounted and used with respect to the handles 14, 150, which are constructed with an appropriate shape corresponding to the type of end effector. Accordingly, without a steep rise in cost of the medical manipulators 10A, 10B, suitable operability can be obtained.

As shown in FIG. 16, the number of times limiting mechanism 70 shown in FIG. 4, etc., is disposed on the handle 150 of the manipulator main body 11B. According to the above configuration, if the number of times that the drive unit 22 has been attached and detached with respect to the handle 150 reaches a predetermined number of times (number of times usage limit of the manipulator main body 11B), by an action of the number of times limiting mechanism 70, it becomes impossible for the drive unit 22 to be attached to the handle 150. Stated otherwise, use of the manipulator main body 11B in excess of the number of times usage limit can be forcibly restricted.

Instead of the number of times limiting mechanism 70, the number of times limiting mechanism 120 according to the modification shown in FIG. 9 may be provided. Further, in this case, the structural example shown in FIG. 13, or the structural example shown in FIGS. 14A and 14B may be adopted.

Although certain preferred embodiments of the present invention have been shown and described in detail above, it should be understood that various changes and modifications may be made to the embodiments without departing from the spirit and scope of the invention as set forth in the appended claims.

What is claimed is:

1. A medical manipulator comprising:
a manipulator main body having a handle;
a drive unit, which is configured to be attached and detached with respect to the handle, and including a drive source; and
a number of times limiting mechanism disposed on the handle, which, in an event that the number of times that the drive unit has been attached and detached with respect to the handle has reached a predetermined number of times, prevents attachment of the drive unit with respect to the handle;
wherein the number of times limiting mechanism includes:
an operating body that is mechanically interlinked with the attachment and detachment of the drive unit with respect to the handle, and
a counter mechanism that is operated by a predetermined amount with each time of operation of the operating body, the counter mechanism including an intermediate transmission mechanism that is driven accompanying operation of the operating body, and a rotating body that is rotated by the intermediate transmission mechanism,
such that when the counter mechanism has been operated the predetermined number of times from an initial state thereof, attachment of the drive unit with respect to the handle is prevented;
wherein the number of times limiting mechanism is configured to be operated from a non-regulating condition to a regulating condition, and includes a stopper that, in the regulating condition, projects into a movement path of the drive unit when the drive unit is attached to the handle;
wherein in a state in which a number of times of attachment and detachment is less than the predetermined number of times, the rotating body engages with the stopper to maintain the non-regulating condition, and in a state in which the number of times of attachment and detachment has reached the predetermined number of times, the rotating body allows the stopper to be changed to the regulating condition;
wherein each of the operating body, the intermediate transmission mechanism, and the rotating body is constituted from a plate-shaped member; and
wherein the stopper is changed from the non-regulating condition to the regulating condition accompanying a tilting movement of the stopper from an initial posture.

2. The medical manipulator according to claim 1, wherein:
the number of times limiting mechanism includes a stopper that is changed to a regulating condition when the counter mechanism has been operated a predetermined number of times from the initial state thereof; and
the stopper, in the regulating condition, projects into a movement path of the drive unit when the drive unit is attached to the handle.

3. The medical manipulator according to claim 1, wherein:
the number of times limiting mechanism includes a lock member that is displaced to a regulating position when the counter mechanism has been operated a predetermined number of times from the initial state thereof; and
the lock member, in the regulating position, prevents movement of the operating body.

4. The medical manipulator according to claim 1, wherein the operating body comprises a slider that is pressed by the drive unit and is displaced from a first position to a second position accompanying attachment of the drive unit with respect to the handle, and returns from the second position to the first position accompanying removal of the drive unit from the handle.

5. The medical manipulator according to claim 4, further comprising an operating body biasing means for biasing the operating body toward the first position.

6. The medical manipulator according to claim 1, wherein the intermediate transmission mechanism includes a plurality of mutually intermeshed gears.

7. The medical manipulator according to claim 1, wherein:
the number of times limiting mechanism includes a stopper biasing member that biases the stopper toward the regulating condition;
a notch is provided in the rotating body;
in a state in which the number of times of attachment and detachment is less than the predetermined number of times, an abutment provided on the stopper abuts against the rotating body, whereby the stopper is retained in the non-regulating condition in opposition to a biasing force of the stopper biasing member; and
in a state in which the number of times of attachment and detachment has reached the predetermined number of times, the abutment provided on the stopper is capable of entering into the notch.

8. The medical manipulator according to claim 1, wherein the intermediate transmission mechanism includes a plurality of mutually intermeshed gears.

* * * * *